US012748102B2

(12) United States Patent
Sances et al.

(10) Patent No.: US 12,748,102 B2
(45) Date of Patent: Sep. 29, 2026

(54) COMPLEX MICROFLUIDIC MODELS FOR ALS INCLUDING NF BIOMARKERS FOR ALS RESEARCH AND DRUG DEVELOPMENT

(71) Applicant: CEDARS-SINAI MEDICAL CENTER, Los Angeles, CA (US)

(72) Inventors: Samuel Sances, Santa Monica, CA (US); Clive Svendsen, Pacific Palisades, CA (US)

(73) Assignee: Cedars-Sinai Medical Center, Los Angeles, CA (US)

(*) Notice: Subject to any disclaimer, the term of this patent is extended or adjusted under 35 U.S.C. 154(b) by 675 days.

(21) Appl. No.: 18/026,907

(22) PCT Filed: Sep. 22, 2021

(86) PCT No.: PCT/US2021/051492
§ 371 (c)(1),
(2) Date: Mar. 17, 2023

(87) PCT Pub. No.: WO2022/066723
PCT Pub. Date: Mar. 31, 2022

(65) Prior Publication Data

US 2023/0333092 A1 Oct. 19, 2023

Related U.S. Application Data

(60) Provisional application No. 63/081,507, filed on Sep. 22, 2020.

(51) Int. Cl.
*G01N 33/50* (2006.01)
*B01L 3/00* (2006.01)
(Continued)

(52) U.S. Cl.
CPC .... *G01N 33/5058* (2013.01); *B01L 3/502715* (2013.01); *C12M 21/08* (2013.01);
(Continued)

(58) Field of Classification Search
None
See application file for complete search history.

(56) References Cited

U.S. PATENT DOCUMENTS

| | | |
|---|---|---|
| 6,300,080 B1 | 10/2001 | Brenner et al. |
| 7,989,197 B2 | 8/2011 | Yoo et al. |

(Continued)

FOREIGN PATENT DOCUMENTS

| | | |
|---|---|---|
| AU | 2015204375 A1 | 8/2015 |
| AU | 2016341880 A1 | 5/2018 |

(Continued)

OTHER PUBLICATIONS

Osaki, Tatsuya; et al; "Microphysiological 3D model of amyotrophic lateral sclerosis (ALS) from human iPS-derived muscle cells and optogenetic motor neurons" Science Advances, 4, eeat5847, 2018 (Year: 2018).*

(Continued)

*Primary Examiner* — David W Berke-Schlessel
(74) *Attorney, Agent, or Firm* — NIXON PEABODY LLP

(57) ABSTRACT

Described herein are the effects of continuous media perfusion on SC-Chips and the observed activation of pronounced neural tissue growth and vascular recruitment into the neural tissue channel. ALS patient chip overexpression of known neurodegenerative disease biomarkers neurogranin and neurofilament family members are also described and utilized for the invention.

22 Claims, 21 Drawing Sheets

(51) Int. Cl.
*C12M 3/00* (2006.01)
*C12N 5/0793* (2010.01)

(52) U.S. Cl.
CPC ....... *C12N 5/0619* (2013.01); *G01N 33/5023* (2013.01); *B01L 2300/0874* (2013.01); *C12N 2501/01* (2013.01); *C12N 2501/13* (2013.01); *C12N 2503/02* (2013.01); *C12N 2506/45* (2013.01); *C12N 2513/00* (2013.01); *C12N 2533/52* (2013.01); *C12N 2533/54* (2013.01); *C12N 2533/90* (2013.01)

(56) References Cited

U.S. PATENT DOCUMENTS

| | | | |
|---|---|---|---|
| 8,647,861 | B2 | 2/2014 | Ingber et al. |
| 9,236,212 | B2 | 1/2016 | Tanaka |
| 9,790,470 | B2 | 10/2017 | Vallier et al. |
| 10,174,289 | B2 | 1/2019 | Wells et al. |
| 11,326,149 | B2 | 5/2022 | Kerns et al. |
| 2004/0247571 | A1 | 12/2004 | Meijer et al. |
| 2007/0077649 | A1 | 4/2007 | Sammak et al. |
| 2007/0128722 | A1 | 6/2007 | Lin |
| 2007/0281353 | A1 | 12/2007 | Vacanti et al. |
| 2008/0044847 | A1 | 2/2008 | Shusta et al. |
| 2008/0132445 | A1 | 6/2008 | Ormandy et al. |
| 2008/0305086 | A1 | 12/2008 | Poole |
| 2009/0075374 | A1 | 3/2009 | Palecek et al. |
| 2009/0123383 | A1 | 5/2009 | Frangioni |
| 2009/0214649 | A1 | 8/2009 | Gazit et al. |
| 2009/0258337 | A1 | 10/2009 | Yagi |
| 2009/0317852 | A1 | 12/2009 | Parker et al. |
| 2009/0324559 | A1 | 12/2009 | Sakurada et al. |
| 2010/0136690 | A1 | 6/2010 | Sundstorm et al. |
| 2011/0064700 | A1 | 3/2011 | Cardozo et al. |
| 2011/0097796 | A1 | 4/2011 | Loa |
| 2011/0111499 | A1 | 5/2011 | Torihashi |
| 2011/0245307 | A1 | 10/2011 | Alkon |
| 2011/0250585 | A1 | 10/2011 | Ingber et al. |
| 2012/0094381 | A1 | 4/2012 | Chambers et al. |
| 2012/0107934 | A1 | 5/2012 | Poole |
| 2012/0128655 | A1 | 5/2012 | Kim et al. |
| 2012/0171354 | A1 | 7/2012 | O'Neill et al. |
| 2012/0196312 | A1 | 8/2012 | Sato et al. |
| 2012/0211373 | A1 | 8/2012 | El-Sayed et al. |
| 2013/0137130 | A1 | 5/2013 | Wells et al. |
| 2013/0224857 | A1 | 8/2013 | Blak et al. |
| 2013/0280802 | A1 | 10/2013 | Schulz et al. |
| 2013/0288969 | A1 | 10/2013 | Scadden |
| 2014/0038279 | A1 | 2/2014 | Ingber et al. |
| 2014/0065660 | A1 | 3/2014 | Hanseup et al. |
| 2014/0093905 | A1 | 4/2014 | Ingber et al. |
| 2014/0134732 | A1 | 5/2014 | Ashton et al. |
| 2014/0142370 | A1 | 5/2014 | Wong et al. |
| 2014/0171380 | A1 | 6/2014 | Kim et al. |
| 2014/0199700 | A1 | 7/2014 | Kume et al. |
| 2014/0248621 | A1 | 9/2014 | Collins |
| 2014/0288093 | A1 | 9/2014 | Krainc et al. |
| 2014/0315990 | A1 | 10/2014 | Alkon et al. |
| 2014/0329321 | A1 | 11/2014 | Rajesh et al. |
| 2014/0342445 | A1 | 11/2014 | Ingber et al. |
| 2015/0017674 | A1 | 1/2015 | Christensen et al. |
| 2015/0023928 | A1 | 1/2015 | Hassiotou |
| 2015/0037320 | A1 | 2/2015 | McGrath et al. |
| 2015/0071874 | A1 | 3/2015 | Han |
| 2015/0151011 | A1 | 6/2015 | Jang et al. |
| 2015/0218522 | A1 | 8/2015 | Peterson et al. |
| 2015/0232810 | A1 | 8/2015 | Luo et al. |
| 2015/0252328 | A1 | 9/2015 | Woodruff et al. |
| 2015/0258124 | A1 | 9/2015 | Katajisto et al. |
| 2015/0265652 | A1 | 9/2015 | George et al. |
| 2015/0329828 | A1 | 11/2015 | Rezania |
| 2016/0145642 | A1 | 5/2016 | Cui et al. |
| 2016/0152950 | A1 | 6/2016 | Zhang et al. |
| 2016/0340633 | A1 | 11/2016 | Davis et al. |
| 2017/0107498 | A1 | 4/2017 | Sareen et al. |
| 2017/0226478 | A1 | 8/2017 | Kerns et al. |
| 2017/0240866 | A1 | 8/2017 | Wells et al. |
| 2017/0253856 | A1 | 9/2017 | Douvaras et al. |
| 2017/0283772 | A1 | 10/2017 | Qian et al. |
| 2017/0292116 | A1 | 10/2017 | Erlls et al. |
| 2017/0313976 | A1 | 11/2017 | Kuwahara et al. |
| 2018/0021383 | A1 | 1/2018 | George et al. |
| 2018/0057788 | A1 | 3/2018 | Kerns et al. |
| 2018/0237741 | A1 | 8/2018 | Gazit et al. |
| 2018/0298331 | A1 | 10/2018 | Kerns et al. |
| 2018/0298332 | A1 | 10/2018 | Kerns et al. |
| 2018/0305651 | A1 | 10/2018 | Kerns et al. |
| 2018/0305668 | A1 | 10/2018 | Gazit et al. |
| 2019/0009270 | A1 | 1/2019 | Gazit et al. |
| 2019/0018000 | A1 | 1/2019 | Gazit et al. |
| 2019/0031992 | A1 | 1/2019 | Kerns et al. |
| 2019/0153395 | A1 | 5/2019 | Barrett et al. |
| 2019/0194606 | A1 | 6/2019 | Vatine et al. |
| 2019/0359924 | A1 | 11/2019 | Kerns et al. |
| 2020/0000267 | A1 | 1/2020 | Zuidervaart et al. |
| 2020/0002671 | A1 | 1/2020 | Qu et al. |
| 2020/0071673 | A1 | 3/2020 | Sareen et al. |
| 2020/0157508 | A1 | 5/2020 | Barrett et al. |
| 2021/0000880 | A1 | 1/2021 | Svendsen et al. |
| 2021/0023039 | A1 | 1/2021 | Laperle et al. |
| 2021/0024886 | A1 | 1/2021 | Laperle et al. |
| 2021/0033628 | A1 | 2/2021 | Laperle et al. |
| 2021/0130774 | A1 | 5/2021 | Sances et al. |
| 2023/0159896 | A1 | 5/2023 | Sharma et al. |
| 2024/0067933 | A1 | 2/2024 | Laperle et al. |
| 2024/0076629 | A1 | 3/2024 | Laperle et al. |
| 2025/0057887 | A1 | 2/2025 | Svendsen et al. |

FOREIGN PATENT DOCUMENTS

| | | | |
|---|---|---|---|
| AU | 2017213795 | A1 | 8/2018 |
| AU | 2017214468 | A1 | 9/2018 |
| AU | 2017319168 | A1 | 3/2019 |
| AU | 2017321489 | A1 | 3/2019 |
| AU | 2018235950 | A1 | 10/2019 |
| AU | 2018236273 | A1 | 10/2019 |
| AU | 2018270270 | A1 | 12/2019 |
| AU | 2017319168 | B2 | 4/2021 |
| AU | 2016341880 | B2 | 5/2021 |
| CA | 3002399 | A1 | 4/2017 |
| CA | 3013337 | A1 | 8/2017 |
| CA | 3013357 | A1 | 8/2017 |
| CA | 3034614 | A1 | 3/2018 |
| CA | 3035058 | A1 | 3/2018 |
| CA | 3055992 | A1 | 9/2018 |
| CA | 3056089 | A1 | 9/2018 |
| CA | 3064086 | A1 | 11/2018 |
| CN | 109642212 | A | 4/2019 |
| EP | 3008168 | A1 | 4/2016 |
| EP | 3031908 | A1 | 6/2016 |
| EP | 3365424 | | 8/2018 |
| EP | 3411470 | A2 | 12/2018 |
| EP | 3411472 | A1 | 12/2018 |
| EP | 3503901 | A1 | 7/2019 |
| EP | 3504319 | A1 | 7/2019 |
| EP | 3625331 | A1 | 3/2020 |
| EP | 3768823 | A1 | 1/2021 |
| EP | 3775161 | A1 | 2/2021 |
| EP | 3787613 | A1 | 3/2021 |
| EP | 3787649 | A1 | 3/2021 |
| EP | 4048282 | | 8/2022 |
| GB | 2561312 | A | 10/2018 |
| GB | 2562406 | A | 11/2018 |
| GB | 2564582 | A | 1/2019 |
| GB | 2568446 | A | 5/2019 |
| GB | 2569058 | A | 6/2019 |
| GB | 2574988 | A | 12/2019 |
| GB | 2575574 | A | 1/2020 |
| GB | 2561312 | B | 3/2021 |
| GB | 2564582 | B | 9/2021 |
| HK | 1260726 | B2 | 7/2021 |
| JP | 2003511346 | A | 9/2000 |
| JP | 2013-537553 | A | 10/2013 |
| JP | 2014-171434 | A | 9/2014 |

(56) References Cited

FOREIGN PATENT DOCUMENTS

| | | | |
|---|---|---|---|
| JP | 2014-528247 | A | 10/2014 |
| JP | 2015-504427 | A | 2/2015 |
| JP | 2015-504676 | A | 2/2015 |
| JP | 2018-533940 | A | 11/2018 |
| JP | 2019-506861 | A | 3/2019 |
| JP | 2021-520784 | A | 8/2021 |
| JP | 2021-523700 | A | 9/2021 |
| JP | 2021-523888 | A | 9/2021 |
| KR | 20180069882 | A | 6/2018 |
| KR | 10-2022-0084282 | | 6/2022 |
| SG | 11201803143 | Y | 5/2018 |
| SG | 11201901621 | A | 3/2019 |
| SG | 11201901628X | | 3/2019 |
| SG | 11201908358 | P | 10/2019 |
| SG | 11201908359 | U | 10/2019 |
| WO | WO 2000053218 | A1 | 9/2000 |
| WO | WO 2005/021720 | A2 | 3/2005 |
| WO | WO 2010/009307 | A2 | 1/2010 |
| WO | WO 2010/108005 | A2 | 9/2010 |
| WO | WO 2011/109440 | A1 | 9/2011 |
| WO | WO 2012/100084 | A1 | 7/2012 |
| WO | WO 2012/118799 | A2 | 9/2012 |
| WO | WO 2013/056216 | A1 | 4/2013 |
| WO | WO 2013/065763 | A1 | 5/2013 |
| WO | WO 2013/071282 | A1 | 5/2013 |
| WO | WO 2013/086486 | A1 | 6/2013 |
| WO | WO 2013/106677 | A1 | 7/2013 |
| WO | WO 2013108926 | A1 | 7/2013 |
| WO | WO 2013/184193 | A2 | 12/2013 |
| WO | WO 2014/159356 | A1 | 10/2014 |
| WO | WO 2014/172682 | A1 | 10/2014 |
| WO | WO 2014/176606 | A1 | 10/2014 |
| WO | WO 2015/052143 | A1 | 4/2015 |
| WO | WO 2015/057261 | A1 | 4/2015 |
| WO | WO 2015/126528 | A1 | 8/2015 |
| WO | WO 2015/138032 | A2 | 9/2015 |
| WO | WO 2015/138034 | A2 | 9/2015 |
| WO | WO 2015/143342 | A1 | 9/2015 |
| WO | WO 2015/153451 | A1 | 10/2015 |
| WO | WO 2015/163823 | A1 | 10/2015 |
| WO | WO 2015/181253 | A1 | 12/2015 |
| WO | WO 2015/183920 | A2 | 12/2015 |
| WO | WO 2015/188131 | A1 | 12/2015 |
| WO | WO 2016/061464 | A1 | 4/2016 |
| WO | WO 2016/063985 | A1 | 4/2016 |
| WO | WO 2016/086040 | A1 | 6/2016 |
| WO | WO 2016/093222 | A1 | 6/2016 |
| WO | WO 2016/141137 | A1 | 9/2016 |
| WO | WO 2016/162747 | A1 | 10/2016 |
| WO | WO 2016/183252 | A1 | 11/2016 |
| WO | WO 2017/035119 | A1 | 3/2017 |
| WO | WO 2017/070224 | A1 | 4/2017 |
| WO | WO 2017/075271 | A1 | 5/2017 |
| WO | WO 2017/078807 | A1 | 5/2017 |
| WO | WO 2017/112455 | A2 | 6/2017 |
| WO | WO 2017/123806 | A1 | 7/2017 |
| WO | WO 2017/136462 | A2 | 8/2017 |
| WO | WO 2017/136479 | A1 | 8/2017 |
| WO | WO 2017/143049 | A1 | 8/2017 |
| WO | WO 2017/200486 | A1 | 11/2017 |
| WO | WO 2017/219000 | A1 | 12/2017 |
| WO | WO 2018/035214 | A1 | 2/2018 |
| WO | WO 2018/044885 | A1 | 3/2018 |
| WO | WO 2018/044934 | A1 | 3/2018 |
| WO | 2018106628 | A1 | 6/2018 |
| WO | WO 2018/140647 | A1 | 8/2018 |
| WO | 2018175574 | A1 | 9/2018 |
| WO | WO 2018/170139 | A1 | 9/2018 |
| WO | WO 2018/170180 | A1 | 9/2018 |
| WO | WO 2018/176001 | A2 | 9/2018 |
| WO | WO 2018/213773 | A1 | 11/2018 |
| WO | 2019023793 | A1 | 2/2019 |
| WO | WO 2019/122291 | A1 | 6/2019 |
| WO | 2019178164 | A1 | 9/2019 |
| WO | WO 2019/178550 | A1 | 9/2019 |
| WO | WO 2019/183597 | A1 | 9/2019 |
| WO | WO 2019169351 | A1 | 9/2019 |
| WO | WO 2019/195798 | A1 | 10/2019 |
| WO | WO 2019/195800 | A1 | 10/2019 |
| WO | WO 2019/212690 | A1 | 11/2019 |
| WO | WO 2019/212691 | A1 | 11/2019 |
| WO | WO 2021/081229 | A1 | 4/2021 |
| WO | WO 2021/081237 | A1 | 4/2021 |
| WO | WO 2021222724 | A1 | 11/2021 |
| WO | WO 2022066723 | A1 | 3/2022 |

OTHER PUBLICATIONS

Osaki, Tatsuya; et al; "Engineered 3D vascular and neuronal networks in a microfluidic platform" Scientific Reports, 8, 5168, 2018 (Year: 2018).*

Shinde, Santosh; et al; "A Complex Network of MicroRNAs Expressed in Brain and Genes Associated with Amyotrophic Lateral Sclerosis" International Journal of Genomics, 383024, 2013 (Year: 2013).*

International Search Report and Written Opinion of PCT/US2017/013250 dated Mar. 31, 2017, 12 Pages.

International Search Report and Written Opinion of PCT/US2016/057724 dated Jan. 9, 2017, 17 Pages.

International Search Report and Written Opinion of PCT/US2017/016098 dated Jun. 22, 2017, 14 Pages.

International Search Report and Written Opinion of PCT/US2017/016079 dated Jul. 25, 2017, 26 Pages.

International Search Report and Written Opinion of PCT/US2017/049193 dated Nov. 6, 2017, 9 Pages.

International Search Report and Written Opinion of PCT/US2017/049115 dated Nov. 28, 2017, 11 Pages.

International Search Report and Written Opinion of PCT/US2018/022511 dated Jul. 26, 2018, 11 Pages.

International Search Report and Written Opinion of PCT/US2018/033498 dated Aug. 9, 2018, 9 Pages.

International Search Report and Written Opinion for PCT/US2018/022455 dated Aug. 23, 2018, 13 pages.

International Search Report and Written Opinion for PCT/US2018/015318 May 2, 2018, 16 pages.

International Search Report and Written Opinion of PCT/US2019/026193 dated Jan. 7, 2019, 8 pages.

International Search Report and Written Opinion of PCT/US2019/026178 dated Jun. 11, 2019, 14 Pages.

International Search Report and Written Opinion of PCT/US2019/026183 dated Jun. 12, 2019, 10 Pages.

International Search Report and Written Opinion of PCT/US2019/026195 dated Jun. 12, 2019, 10 pages.

International Search Report and Written Opinion of PCT/US2019/023749 dated Jun. 25, 2019, 12 Pages.

International Search Report and Written Opinion for PCT/US2018/024198 dated Aug. 13, 2018, 15 pages.

International Search Report and Written Opinion for PCT/US2020/056896 dated Oct. 22, 2020, 11 pages.

International Search Report and Written Opinion for PCT/US2020/056906 dated Mar. 16, 2021, 13 pages.

International Preliminary Report on Patentability for PCT/US2016/057724 dated Apr. 24, 2018, 15 pages.

International Preliminary Report on Patentability for PCT/US2017/013250 dated Jul. 17, 2018, 7 pages.

International Preliminary Report on Patentability for PCT/US2017/016098 dated Aug. 7, 2018, 10 pages.

International Preliminary Report on Patentability for PCT/US2017/016079 dated Aug. 7, 2018, 21 pages.

International Preliminary Report on Patentability for PCT/US2018/022511, dated Sep. 17, 2019, 8 pages.

International Preliminary Report on Patentability for PCT/US2018/022455 dated Aug. 23, 2018, 9 pages.

International Preliminary Report on Patentability for PCT/US2018/033498 dated Nov. 19, 2019, 8 pages.

International Preliminary Report on Patentability for PCT/US2017/049193 dated Mar. 5, 2019, 8 pages.

(56) References Cited

OTHER PUBLICATIONS

International Preliminary Report on Patentability for PCT/US2017/049115 dated Mar. 5, 2019, 8 pages.
International Preliminary Report on Patentability for PCT/US2018/015318 dated Jul. 30, 2019, 12 pages.
International Preliminary Report on Patentability for PCT/US2018/024198 dated Feb. 25, 2020, 12 pages.
AU 2016341880 Examination Report dated Jan. 15, 2020, 5 pages.
AU 2017214468 Examination Report dated Dec. 10, 2019, 5 pages.
CA 3034614 Examination Report dated Jul. 5, 2019, 5 pages.
EP 16858141.1 Extended Search Report dated Mar. 15, 2019, 10 pages.
EP 17748100.9 European Partial Supplementary Search Report dated Sep. 18, 2019, 15 pages.
EP 17748100.9 European Extended Search Report dated Dec. 20, 2019, 12 pages.
EP 17748084.5 European Extended Search Report dated Sep. 10, 2019.
EP 17847396.3 European Extended Search Report dated, Jan. 28, 2020, 11 pages.
EP17847365.8 European Extended Search Report dated Jan. 21, 2020, 11 pages.
EP 19782199.4 Partial Supplementary Search Report dated Nov. 30, 2021, 15 pages.
EP 19796470.3 European Extended Search Report dated Dec. 10, 2021, 11 pages.
EP 19771249.0 Partial Supplemental European Search Report dated Nov. 8, 2011, 15 pages.
EP 18802136.4 Examination Report dated Oct. 14, 2021, 8 pages.
EP 18802136.4 Extended European Search Report dated Jan. 22, 2021, 12 pages.
EP 19782199.4 Extended European Search Report dated Mar. 3, 2022, 12 pages.
EP 19796911.6 Extended Search Report dated Apr. 29, 2022, 15 pages.
EP 21873328.5 Extended European Search Report dated Sep. 5, 2024, 9 pages.
GB1811716.8 Examination Report dated Feb. 12, 2020, 6 pages.
GB 1903007.1 Search Report dated Apr. 1, 2019, 8 pages.
GB 1903007.1 Search Report dated Jun. 24, 2020, 3 pages.
JP 2018-540028 Notice of Reasons for Rejection dated Mar. 1, 2021.
JP Reasons for Rejection-2020-560893 dated Feb. 6, 2023, 9 pages.
SG 11201803143Y Search Report dated Jul. 15, 2019, 3 pages.
SG 11201901628X Written Opinion dated Mar. 10, 2021, 9 pages.
Abbott et al., Structure and function of the blood-brain barrier, Neurobiology of Desease, 2010 27:13-25.
Abbott et al., Structure and function of the blood-brain barrier, Pharm Tox BBB: 1-3, Feb. 2010, Conf. Abstract.
Action Potential, Wikipedia, pp. 1-29 Downloaded on Apr. 28, 2019, https://en.wikipedia.org/wiki/Action_potential.
Adriani et al., Modeling the Blood-Brain Barrier in a 3D Triple Co-Culture Microfluidic System, 37th Annual International Conference of the IEEE Engineering in Medicine and Biology Society, IEEE, pp. 338-341.
Akhtar et al., Inducible Expression of GDNF in Transplanted iPSC-Derived Nueral Progenitor Cells, Stem Cell Reports, 2018, vol. 10, pp. 1696-1704.
Amoroso M. W et al., Accelerated High-Yield Generation of Limb-Innervating Motor Neurons from Human Stem Cells. J Neurosci, Jan. 9, 2013, vol. 33, No. 2, pp. 574-586 pp. 575 and 578, Fig. 1 and 2.
Araoka, et al., Efficient and rapid induction of human iPSCs/ESCs into nephrogenic intermediate mesoderm using small molecule-based differentiation methods, PLoS One, 2014, 9(1), 14 pages.
Arendt et al., Form and Function: how Estrogen and Progesterone Regulate the Mammary Epithelial Hierarchy, J. Mammary Gland Biol Neoplasia, 2015, 20:9-25.
Armstrong et al., Human Induced Pluripotent Stem Cell Lines Show Stress Defense Mechanisms and Mitochondrial Regulation Similar to Those of Human Embryonic Stem Cells, 2010, Stem Cells, vol. 28(4), pp. 661-673.
Badger et al., Parkinson's disease in a dish Using stem cells as a molecular tool, Neuropharmacology, 2014, vol. 76, Abstract Only.
Bai et al., BMP-2, Vegf and bFGF Synergistically Promote the Osteogenic Differentiation of Rat Bone Marrow-Derived Mesenchymal Stem Cells, Biotechnol Lett, 2013, vol. 35, pp. 301-308.
Bar-Am et al., Regulation of protein kinase C by the anti-Parkinson drug, MAO-B inhibitor, rasagiline and its derivatives, in vivo, Journal of Neurochemistry, 2004, vol. 89, No. 5, pp. 1119-1125.
Barrett et al., Reliable Generation of Induced Pluripotent Stem Cells from Human Pymphoblastoid Cell Lines, 2014, Stem Cells Translational Medicine, vol. 3, pp. 1429-1434.
Ben-Zvi et al., Modeling Human Nutrition Using Human Embryonic Stem Cells, Cell, 2015, vol. 161(1), pp. 12-17.
Bhatia et al., Microfluidic Organs-on-Chips, Nature Biotechnology, 2014, vol. 32(8), pp. 760-772.
Bohrnsen et al. Supportive angiogenic and osteogenic differentiation of mesenchymal stromal cells and endothelial cells in monolayer and co-cultures. International Journal of Oral Science (2016) 8, 223-230 (Year: 2016).
Booth, Ross Hunter, A Microfluidic in Vitro Model of the Blood-Brain Barrier, Dissertation, 2014, pp. 1-177.
Boyer et al., More than a Bystander: The Contributions of Intrinsic Skeletal Muscle Defects in Motor Neuron Diseases, 2013, Frontiers in Physiology, vol. 4, Article 356, pp. 1-12.
Brittan et al., The gastrointestial stem cell, Cell Prolif., 2004, vol. 37, pp. 35-53.
Brown et al., Recreating Blood-Brain Barrier Physiology and Structure on Chip: A Novel Neurovascular Microfluidic Bioreactor, 2015, Biomicrofluidics, vol. 9(5).
Burkhardt et al., A Cellular Model for Sporadic ALS using Patient-Derived Induced Pluripotent Stem Cells, Molecular and Cellular Neuroscience, 2013, vol. 56, pp. 355-364.
Cashman et al., Induced Pluripotent Stem Cells and Motor Neuron Disease: Toward an Era of Individualized Medicine, J. Neurosci, 2013, vol. 33, pp. 8587-8589.
Chal et al., Differentiation of Pluripotent Stem Cells to Muscle Fiber to Model Duchenne Muscular Dystrophy, 2015, Nature Biotechnology, vol. 33(9), pp. 962-969.
Chen, et al., Chemically defined conditions for human iPSC derivation and culture, 2011, Nat. Methods, 8(5), 8 pages.
Chen et al., Surface Marker Epithelial Cell Adhesion Molecule and E-Cadherin Facilitate the Identification and Selection of Induced Pluripotent Stem Cells, 2011, Stem Cell Rev., vol. 7(3), pp. 722-735.
Chou et al., Efficient human iPS cell derivation by a non-integrating plasmid from blood cells with unique epigenetic and gene expression signatures, Cell Research, 2011, 21:3, pp. 518-529.
Clayton, et al., Generating induced pluripotent stem cell derived endothelial cells and induced endothelial cells for cardiovascular disease modelling and therapeutic angiogenesis, International Journal of Cardiology 197: 116-122. doi: 10.1016/ j.ijcard.2015.06.038. (Year: 2015).
Cooper et al., Differentiation of human ES and Parkinson's disease iPS cells into ventral midbrain dopaminergic neurons requires a high activity form of SHH, FGF8a and specific regionalization by retinoic acid, Molecular and Cellular Neurosciences, 2010, vol. 45, No. 3, pp. 258-266.
Danmark et al., Development of a novel microfluidic device for long-term in situ monitoring of live cells in 3-dimensional matrices, Biomed Microdevices, 2012, pp. 885-893.
Date et al., Mini-Gut Organoids: Reconstruction of the Stem Cell Niche, Annu. Rev. Cell Dev. Biol., 2015, vol. 31, pp. 269-289.
Demers et al., Development-on-Chip: in vitro Neutral Tube Patterning with a Microfluidic Device, Development, 2016, vol. 143(11), pp. 1884-1892.
Dhumpa et al., Temporal Gradients in Microfluidic Systems to Probe Cellular Dynamics: A Review, Anal. Chim. Acta, 2012, vol. 743, pp. 9-18.

(56) References Cited

OTHER PUBLICATIONS

Dimos et al., Induced Pluripotent Stem Cells Generated from Patients with ALS can be Differentiated into Motor Nuerons, Science, 2008, vol. 321, pp. 1218-1221.
Douville et al., Fabrication of Two-Layered Channel System with Embedded Electrodes to Measure Resistance Across Epithelial and Endothelial Barriers, 2010, Analytical Chemistry, vol. 82(6), pp. 2505-2511.
Ebert et al., EZ Spheres: A Stable and Expandable Culture System for the Generation of Pre-rosette Multipotent Stem Cells from Human ESCs and iPSCs., 2013, Stem Cell Research, vol. 10(3), pp. 417-427.
Esch et al., Organs-on-Chips at the Frontiers of Drig Discovery, Nature Reviews, 2015, vol. 14(4), pp. 248-269.
Evans et al., The Development of a Method for the Preparation of Rat Intestinal Epithelial Cell Primary Cultures, 1992, Journal of Cell Science, vol. 101, pp. 219-231.
Faravelli I. et al., Motor neuron derivation from human embryonic and induced pluripotent stem cells: Experimental approaches and clinical perspectives. Stem Cell Res Ther, Jul. 14, 2014, vol. 5, No. 4, p. 87.
Farrelly et al., Extracellular matrix regulates apoptosis in mammary epithelium through a control on insulin signaling, The Journal of Cell Biology, 1999, 144(6): 1337-1347.
Fridley et al., Hydrodynamic modulation of pluripotent stem cells, Stem cell research & therapy,2012, vol. 45.
Gao et al., Regulation of Cell Migration and Osteogenic Differentiation in Mesenchymal Stem Cells under Extremely Low Fluidic Shear Stress, Biomicrofluidics, 2014, vol. 8(5), Article No. 052008.
Gel, Wikipedia, pp. 1-29 Downloaded on Sep. 14, 2018, https://en.wikipedia.org/wiki/Gel.
Gracz et al., CD24 and CD44 Mark Human Intestinal Epithelial Cell Populations with Characteristics of Active and Facultative Stem Cells, 2013, Stem Cells, vol. 31(9), pp. 2024-2030.
Gross et al., Applications of Microfluidics for Neuronal Studies, 2007, Journal of the Neurological Sciences, vol. 252, pp. 135-143.
Gurusamy et al., Hepatocyte Growth Factor-Like Protein is a Positive Regulator of Early Mammary Gland Ductal Morphogenesis, Mechanisms of Development, 2014, vol. 133, pp. 11-22.
Hayes et al., Strategies to generate induced pluripotentstem cells, Methods in Molecular Biology 1029: 77-92. doi: 10.1007/978-1-62703-478-4_6 (Year: 2013).
Hens et al., BMP4 and PTHrP interact to stimulate ductal outgrowth during embryonic mammary development and to inhibit hair follicle induction, Development, 2007, 134:1221-1230.
Hoveizi et al., Differential effect of Activin A and WNT3a on definitive endoderm differentiation on electrospun nanofibrous PCL scaffold, Cell Biology International, 2015, 9999, pp. 1-9.
Hojo et al., Development of high-throughput screening system for osteogenic drugs using a cell-based sensor, Biochemical and Biophysical Research Communiatins 376(2):375-379, 2008.
Hu et al. Neural differentiation of human induced pluripotent stem cells follows developmental principles but with variable potency, PNAS, 2010, vol. 107(9), pp. 4335-4340.
Hu et al., Derivation, Expansion and Motor Neuron Differentiation of Human-Induced PluripotentStem Cells with Non-Integrating Episomal Vectors and a Defined Xenogeneic-Free Culture System, Mol Neurobiol, 2016, vol. 53, pp. 1589-1600.
Hughes et al., Matrigel: A Complex Protein Mixture Required for Optimal Growth of Cell Culture, 2010, Proteomics, vol. 10, pp. 1886-1890.
Huh et al., From 3D Cell Culture to Organs-on-Chips, Trends in Cell Biology, 2011, vol. 21(2), pp. 745-754.
Huh et al., Microfabrication of Human Organs-on-Chips, Nature Protocols, 2013, vol. 8(11), pp. 2135-2157.
Hynds et al., Concise Review: The Relevance of Human Stem Cell-Derived Organoid Models for Epithelial Transitional Medicine, Stem Cells, 2013, vol. 131, pp. 417-422.
Ichida et al., Probing disorders of the nervous system using reprogramming approaches, Theembo Journal / European Molecular Biology Organization, 2015, vol. 34, No. 11, pp. 1456-1477.
Jang et al., JAK-STAT Pathway and Myogenic Differentiation, JAKSTAT, 2013, vol. 2(2), pp. e23282-1 to e-23282-6.
Jenke et al., DNA Methylation Analysis in the Intestinal Epithelium—Effect of Cell Separation on Gene Expression an Methylation Profile, PLOS One, 2013, vol. 8(2), pp. 1-8.
Jha et al., Motor Neuron differentiation from Pluripotent Stem Cells and Other IntermediateProliferative Precursors that can be Discriminated by Lineage Specific Reports, Stem Cell Rev Rep, Aug. 2014, 11:194-204.
Joo-Eun, L., Patient-Specific Induced Pluripotent Stem Cell Models of Variant Angina Derived fromPeripheral Blood, The Department of Biomedical Sciences Seoul National University College of Medicine, Jul. 2017, pp. 1-75.
Kauffman et al., Alternative functional in vitro models of human intestinal epithelia, frontiers in Pharmacology, Jul. 2013, vol. 4, Article 79, 18 pages.
Kelamangalath et al. k-Opioid receptor inhibition of calcium oscillations in spinal cord neurons,, Molecular Pharmacology, 2011, 79:1061-1071.
Kessler et al., The Notch and Wnt pathways Regulate Stemness and Differentiation in Human Fallopian Tube Organoids, Nature Communications, 2015, vol. 6, p. 8989.
Kilic et al., Brain-on-a-Chip Model Enables Analysis of Human Neuronal Differentiation and Chemotaxis, 2016, Lab on a Chip, vol. 16(21), pp. 4152-4162.
Kilpatrick, K. et al., Genetic and chemical activation of TFEB mediates clearance of aggregated a-synuclein, PLoS One, 2015, 10:3, pp. 1-21.
Kim, et al. [3-Cell regeneration through the transdifferentiation of pancreatic cells: Pancreaticprogenitor cells in the pancreas, Journal of Diabetes Investigation 7(3): 286-296. doi: 10.1111/jdi.12475. (Year: 2016).
Kim et al. A practical guide to microfluidic perfusion culture of adherent mammalian cells. Lab Chip, 2007, 7, 681-694 (Year: 2007).
Kim et al., Human Gut-on-a-Chip Inhabited by a Microbial Flora that Experiences Intestinal Peristalsis-Like Motions and Flow, Lab on a Chip, 2012, vol. 12(12). p. 2165.
Kim et al., Gut-on-a-Chip Microenvironmental Induces Human Intestinal Cells to Undergo Villus Differentiation, Integrative Biology, 2013, vol. 5(9), p. 1130-1140.
Kim et al. Shear Stress Induced by an Interstitial Level of Slow Flow Increases the OsteogenicDifferentiation of Mesenchymal Stem Cells through TAZ Activation. PLoS One 9(3): e92427. p. 1-9 (Year: 2014).
Kim et al., Contributions of Microbiome and Mechanical Deformation to Intestinal Bacterial Overgrowth and Inflammation in a Human Gut-on-a-Chip, PNAS, 2015, vol. 113(1), pp. E7-E15.
Kirkby et al., A Role for Correlated Spontaneous Activity in the Assembly of Neural Circuits, 2013, Neuron, vol. 80(5), 27 Pages.
Kitamura et al., Possible Involvement of Both Mitochondria and Endoplasmic Reticulum-Dependent Caspase Pathways in Retenone-Induced Apoptosis in Human Neuroblastoma SH-SY5Y Cells, Neuroscience Letters, 2002, vol. 2002, pp. 25-28.
Kondo et al., Ipsc-based compound screening and in vitro trials identify a synergistic anti-amyloid b combination for Alzheimer's Disease, Cell Reports, 2017, vol. 21, pp. 2304-2312.
Kreke et al. Effect of Intermittent Shear Stress on Mechanotransductive Signaling and OsteoblasticDifferentiation of Bone Marrow Stromal Cells. Tissue Engineering: Part A vol. 14, No. 4, 2008. p. 529-537 (Year: 2008).
Kuratnik et al., Intestinal organoids at tissue surrogates for toxicological and pharmacological studies, biochemical Pharmacology, Apr. 25, 2013, vol. 85:12, pp. 1721-1726.
Kwasny et al., Static biofilm cultures of gram-positive pathogens grown in a microtiter format used for anti-biofilm drug discovery, Current Protocols in Pharmacology, 2010, 13A.8.1-13A.8.23.
Lee et al. Microfluidic 3D bone tissue model for high-throughput evaluation of would healing and infection-preventing biomaterials, Biomaterials 33.4 2012 999-1006.

(56) References Cited

OTHER PUBLICATIONS

Lenner, J., Fat Cells More Easily Programmed into iPS Cells, 2009, pp. 1-2.
Lenzi et al., Differentiation of Control and ALS Mutant Human iPSCs into Functional SkeletalMuscle Cells, A Tool for the Study of Neuromuscolar Diseases, Stem Cell Research, 2016, vol. 17, pp. 140-147.
Levanon, et al., Primary ex vivo cultures of human fallopian tube epithelium as a model for serous ovarian carcinogenesis, Oncogene, 2010, 29(8):1103-1113.
Li et al., Protein kinase C controls lysosome biogenesis independently of mTORC1, Nature Cell Biology, 2016, 10:10, pp. 1-26.
Lin et al., Embryoid body formation from human pluripotent stem cells in chemically defined E8 media, StemBook, ed, Jun. 1, 2014.
Lin et al., Neural Stem Cell Differentiation in a Cell-Collagen-Bioreactor Culture System, 2004, Developmental Brain Research, vol. 153, pp. 163-173.
Lippmann, et al., Human Blood-Brain Barrier Endothelial Cells Derived from Pluripotent Stem Cells, 2012, Nature Biotechnology, vol. 30(8), pp. 783-791.
Lippmann et al., A Retinoic Acid-Enhanced, Multicellular Human Blood-Brain Barrier Model Derived from Stem Cell Sources, Scientific Reports, vol. 4(1), 2014, pp. 1-10.
Lippmann et al., Chemically Defined Differentiation of Human Pluripotent Stem Cells to Hindbrain and Spinal Cord Neural Stem Cells with Defined Regional Identifies, 2015, Protocol Exchange.
Loo et al., An Arduous Journey from Human Pluripotent Stem Cells to Functional Pancreatic Beta Cells, Diabetes Obes Metab., 2018, vol. 20(3), pp. 3-13.
Maegawa et al. Enhancement of osteoblastic differentiation of mesenchymal stromal cells cultured byselective combination of bone morphogenetic protein-2 (BMP-2) and fibroblast growth factor-2 (FGF-2). J Tissue Eng Regen Med 2007; 1: 306-313 (Year: 2007) Abstract Only.
Martin et al., Laparoscopic Colorectal Resection in the Obese Patient, 2011, Clinics in Colon and Rectal Surgery, vol. 24(4), pp. 263-273.
Massumi et al., Efficient Programming of Human Eye Conjunctiva-Derived Induced PluripotentStem (ECiPS) Cells into Definitive Endoderm-Like Cells, Experimental Cell Research, 2014, vol. 322, pp. 51-61.
Matsumoto et al., Functional neurons generated from T Cell-derived induced pluripotent stem cells for neurological disease modeling, 2016, 6:422-435.
Mcgaugh et al., Efficient Differentiation of Pluripotent Stem Cells to NKX6-1 + Pancreating Progenitors, Journal of Visualized Experiments, 2017, vol. 121, pp. 1-5.
Mckinney, C.E et al., Using induced pluripotent stem cells derived neurons to model brain diseases, Neural Regeneration Research, 2017, 12:7 pp. 1-11.
Moors et al., Therapeutic potential of autophagy-enhancing agents in Parkinson's disease, Molecular Neurodegeneration, 2017, 12:11, p. 1-18.
Munera et al., Differentiation of Human Pluripotent Stem Cells into Colonic Organoids via Transient Activation of BMP Signaling, Cell Stem Cell, 21, 51-64, 2017.
Murphy et al., Scaffolds for 3D in vitro Culture of Neural Lineage Cells, Acta Biomaterialia, 2017, vol. 54, pp. 1-20.
Myotube, Medical Dictionary—Downloaded on Jul. 8, 2018, https://medical-dictionary.thefreedictionary.com/myotube, p. 1.
Naik et al., In vitro blood-brain models: Current and perspective technologies, J. Phar Sci., 2012, 1014(4): 1337-1354.
Nicoleau et al., Embryonic Stem Cells Neural Differentiation Qualifies the Role of Wnt/[beta]-Catenin Signals in Human Telecephalic Specification and Regionalization: Human ESC Telencephalic Differentiation, Stem Cells, 2013, vol. 31(9), pp. 1763-1774.
Niego et al., Improved Method for the Preparation of a Human Cell-based, Contact Model of the Blood-Brain Barrier, 2013, J. Vis. Exp., vol. 81(e50934), pp. 1-9.
Nishimura et al. Effect of osteogenic differentiation medium on proliferation and differentiation ofhuman mesenchymal stem cells in threedimensional culture with radial flow bioreactor. Regenerative Therapy 2 (2015) 24-31 (Year: 2015).
Nostro et al., Efficient Generation of NKX6-1+ Pancreatic Progenitors from Multiple Human Pluripotent Stem Cell Lines, Stem Cell Reports, 2015 4(4), pp. 591-604.
Oceguera-Yanez et al., Engineering the AAVS1 locus for consistent and scalable transgene expression in human IPSCs and their differentiated derivatives, Methods, 2016, 1:43-55.
Ochetta et al., High-Throughput Microfluidic Platform for 3D Cultures of Mesenchymal StemCells, Towards Engineering Developmental Processes, Scientific Reports, 2015, vol. 5, Article No. 10288, pp. 1-12.
Okita et al., A More Efficient Method to Generate Integration-Free Human iPS Cells, 2011, Nature Methods, vol. 8(5), pp. 409-412.
Okita et al., An efficient nonviral method to generate integration-free human-induced pluripotent stem cells from cord blood and peripheral blood cells, Stem Cells 2013, 31:458-466.
O'Neill et al., Genetic disorders coupled to ROS deficiency, Redox Biology, 6: 135-156. (Year: 2015).
Ong et al., A Gel-Free 3D Microfluidic Cell Culture System, Biomaterials, 2008, vol. 29, pp. 3237-3244.
Park et al., Chip-Based Comparison of the Osteogenesis of Human Bone Marrow and AdiposeTissue-Derived Mesenchymal Stem Cells under Mechanical Stimulation, PLOS One, 2012, vol. 7(9), pp. 1-12.
Perry et al., The Neuromuscular junction: Structure and function, downloaded from the internet (Neuromuscular junction: Parts, structure and steps/Kenhub>, pp. 1-6, downloaded Feb. 25, 2021.
Polini et al., Organs-on-a-Chip: A New Tool for Drug Discovery, Expert Opinion on Drug Discovery, 2014, vol. 9(4), pp. 335-352.
Polydimethylsiloxane-Wikipedia, dowloaded on Feb. 24, 21 <Silicon dioxide—Wikipedia>, pp. 1-11.
Prabhakarpandian et al., SyM-BBB: A Microfluidic Blood Brain Barrier Model, Lab on a Chip, 2013, vol. 13(6), p. 1093.
Qian et al., A Simple and Efficient System for Regulating Gene Expression in Human Pluripotent Stem Cells and Derivatives, Stem Cells, 2014, vol. 32(5), pp. 1230-1238.
Qiao et al., AP2y regulates neural and epiderman development downstream of the BMP pathway at early stages of ectodermal patterning, Cell Research, 2012, 22:1546-1561.
Qu et al., Differentiation of human induced pluripotent stem cells to mammary-like organoids, Stem Cell Reports, 2017, 8(2):205-215.
Rajesh et al., Human Lymphoblastoid B-Cell Lines Reprogrammed to EBV-FREE Induced Pluripotent Stem Cells, 2011, Blood, vol. 118(7), pp. 1797-1800.
Recchia et al., a-Synuclein and Parkinson's disease, The FASEB Journal, 2004, 18:617-626.
Rey, et al., Chapter 7, Sexual Differentiation, 2016 [online]. [Retrieved on Sep. 19, 2019].Retrieved from the internet <URL:https://www.endotext.org/wp-content/uploads/pdfs/sexual-differentiation.pdf>, 89 pages.
Rhee et al., Patterned Cell Culture Inside Microfluidic Devices, Lab Chip, 2005, vol. 5(1), pp. 102-107.
Roberts et al., Expression of the Thyroid Hormone Transports Monocarboxylate Transporter-8(SLC16A2) and Organic Ion Transporter-14 (SLCO1C1) at the Blood-Brain Barrier, Endocrinol, 2008, vol. 149(12), pp. 6251-6261.
Rosenberg et al., Calcium Signaling in Neuronal Development, 2011, Cold Spring Harb Perspect Biol., vol. 3(a004259), 13 Pages.
Ryan et al., Progranulin is expressed within motor neurons and promotes neuronal cell survival, BMC Neuroscience, 2009, 10:130, pp. 1-22.
Ryan et al., Isogenic Human iPSC Parkinson's Model Shows Nitrosative Stress-Induced Dysfunction in MEF2-PGCI[alpha] Transcription, Cell, 2013, vol. 155, No. 6, pp. 1351-1364.
Sanchez-Danes et al., Disease-specific phenotypes in dopaminemodels of genetic and sporadic Parkinson's disease, EMBO No. 5, pp. 380-395.
Sances et al., Modeling ALS with Motor Neurons Derived from Human Induced Pluripotent Stem Cells, Nature Neuroscience , 2016, vol. 19, pp. 542-553.

(56) References Cited

OTHER PUBLICATIONS

Santaguida et al., Side By Side Comparison Between Dynamic Versus Static Models of Blood-Brain-Barrier in vitro: A Permeability Study, Brain Research, 2006, vol. 1109(1), pp. 1-13.
Sareen et al., Human Neural Progenitor Cells Generated from Induced Pluripotent Stem Cells canSurvive, Migrate, and Integrate in the Rodent Spinal Cord, Journal of Comparative Neurology, 2014, vol. 522(12), pp. 2707-2728.
Sareen et al., Targeting RNA foci in iPSC-Derived Motor Neurons from ALS Patients with C90RF72 Repeat Expansion, 2013, Science Translational Medicine, vol. 5(208), 208ra149, 26 Pages.
Schiesser et al., Derivation of Insulin-Producing Beta-Cells from Human Pluripotent Stem Cells, The Review of Diabetic Studies, 2014, vol. 11(1), pp. 6-18.
Schwartz et al., Allan-Herndon-Dudley Syndrome and the Monocarboxylate Transporter 8 (MCT8) Gene, 2005, AJHG, vol. 77(1), pp. 41-53.
Shafa et al., Human-Induced Pluripotent Stem Cells Manufactured Using a Current GoodManufacturing Practice-Compliant Process Differentiate Into Clinically Relevant Cells From Three Germ Layers, Frontiers in Medicine 5: 69. doi: 10.3389/fmed.
Shimuzu et al., Microfluidic Devices for Construction of Contractile Skeletal Muscle Microtissues, J. Biosci. Bioeng., 2015, vol. 119, pp. 212-216.
Shimojo et al., Rapid, Efficient and Simple Motor Neuron Differentiation from Human Pluripotent Stem Cells, Molecular Brain, 2015, vol. 8(1), pp. 1-15.
Silicon dioxide-Wikipedia, downloaded on Feb. 24, 2021 <silicon dioxide—Wikipedia> pp. 1-20.
Simeone et al., The Otx Family, Pattern Formation and Development Mechanisms, 2002, vol. 12, pp. 409-415.
Soria-Valles et al., NF-kB Activation Impairs Somatic Cell Reprogramming in Ageing, 2015, Nat. Cell Biol., vol. 17(8), pp. 1004-1013.
Southam et al., Microfluidic primary culture model of the lower motor neuron-neuromuscular junction circuit, J Neurosc Meth 2013, 218:164-169.
Southam et al., A Novel in vitro Primary Culture Model of the Lower Motor Neuron-Nueromuscular Junction Circuit, Microfludic and Compartmentalized Platforms for Neurobiological Research, Humana Press, 2015, pp. 181-193, abstract only.
Stepniewski et al., Induced Pluripotent Stem Cells as a Model for Diabetes Investigation, Scientific Reports, 2015, 5:8597, 14 pages.
Sun et al., Role of Bone Morphogenetic Protein-2 in Osteogenic Differentiation of MesenChymal Stem Cells, Molecular Medicine Reports, 2015, vol. 12, pp. 4230-4237.
Sundberg et al., Improved cell therapy protocol for Parkinson's Disease based on differentiationefficiency and safety of Hesc-, Hipsc and non-human primate Ipsc-derived DA neurons, Stem Cells, 2013, 31:8, pp. 1-25.
Telias et al., Electrical Maturation of Neurons Derived from Human Embryonic Stem Cells, F1000 Research, 2014, vol. 3(196), p. 1-12.
Tenstad et al., Extensive Adipogenic and Osteogenic Differentiation of Patterned HumanMesenchymal Stem Cells in a Microfluidic Device, Lab on a Chip, 2010, vol. 10(11), pp. 1401-1409.
Tian et al., Salvianolic Acid B, An Antioxidant from Saliva Miltiorrhiza, prevents 6-hydroxydopamine Induced Apoptosis in SH-SY5Y Cells, The International Science Journal of Biochemistry & Cell Biology, 2008, vol. 40, pp. 409-422.
Uzel et al., New Microfluidic Chip Replicates Muscle-Nerve Connection, 2016, Science Daily, pp. 1-4.
Uzel et al., Microfluidic Device for the Formation of Optically Excitable, Three-Dimensional, Compartmentalized Motor Units, Science Advances, 2016, p. e1501429.
Vatine et al., Human iPSC-Derived Blood-Brain Barrier Chips Enable Disease Modeling and Personalized Medicine Applications, Cell Stem Cell, 2019, vol. 24(6), pp. 995-1005.
Vatine et al., Human iPSC-Derived Blood-Brain Barrier Chips Enable Disease Modeling and Personalized Medicine Applications, Cell Stem Cell, 2019, vol. 24, Supplemental Figures, p. 1-10.
Vogel, et al., Co-culture of human induced pluripotent stem cells 9iPSCs) with human fallopian tubeepithelium (FTE) induces Pax8 and CK7 expression: Initial steps in modeling fallopian tube epithelium to study serous carcinogenesis; Gynecologic Oncology, 2015 137(1):206.
Wang et al., Microfluidics: A new cosset for neurobiology, Lab Chip, 2009, 9:644-652.
Wang et al., Androgen Receptor-Mediated Apoptosis in Bovine Testicular Induced Pluripotent Stem Cells in Response to Phthalate Esters, 2013, Cell Death Dis., vol. 4(e907), pp. 1-11.
Wang et al., Modeling the Mitochondrial Cardiomyopathy of Barth Syndrome with InducedPluripotent Stem Cell and Heart-on-Chip Technologies, Nature Medicine, 2014, vol. 20(6), pp. 616-623.
Wang et al., Generation of an Induced Pluripotent Stem Cell Line (SHCDNi003-A) from a One-YearOld Chinese Han Infant with Allan-Herndon-Dudley Syndrome, Stem Cell Research, 2020, vol. 46, 4 pages.
Watson et al., Modelling the Endothelial Blood-CNS Barriers: A Method for the Production ofRobust in Vitro Models of the Rat Blood-Brain Barrier and Blood-Spinal Cord Barrier, 2013, BMC Neuroscience, vol. 14(59), pp. 1-21.
Wehkamp et al., Reduced Paneth Cell [alpha]-Defensins in Ileal Crohn's Disease, PNAS, 2005, vol. 102, pp. 18129-18134.
Wu et al., Nuclear Accumulation of Histone Deacetylase 4 (HDAC4) Exerts Neurotoxicity in Models of Parkinson's Disease, Moi Neurobiol, 2017, vol. 54, pp. 6970-6983.
Workman et al., Intestine-Chip: A new model to understand the role of the Intestinal Epithelium inIBD by combining Microengineering Technology and IPSC-Derived human intestinal organoids, Gastroenterology, Apr. 1, 2017, vol. 152:5, Abstract only.
Workman et al., Enhanced Utilization of Induced Pluripotent Stem Cell-Derived Human IntestinalOrganoids Using Microengineered Chips, CMGH Cellular and Molecular Gastroenterology and Hepatology, 2018, vol. 5(4), pp. 669-677.
Yamamoto et al., Fluid Shear Stress Induces Differentiation of Flk-1-positive Embryonic StemCells into Vascular Endothelial Cells in vitro., 2004, Am. J. Physiol. Heart Circ. Physiol., vol. 288, pp. 1915-1924.
Yamamoto et al., The Stabilization Effect of Mesenchymal Stem Cells on the Formation ofMicrovascular Networks in a Microfluidic Device, Journal of Biomechanical Science and Engineering, 2013, vol. 8(2).
Yang et al., From the vascular microenvironment to neurogenesis, Brain Res Bull. Jan. 15, 2011; 84(1): 1-7.
Yuan et al., Overexpression of a-Synuclein down-regulates BDNF Expression, Cell and Molecular Neurobiology, 2010, 30:939-946.
Yu et al., A Microfluidic-Based Multi-Shear Device for Investigating the Effects of Low Fluid- Induced Stresses on Osteoblasts, PLOS One, 2014, vol. 9(2), pp. 1-7.
Zhang et al., Regulation and Patterning of Cell Differentiation and Pluripotency, Thesis, Columbia University, pp. 1-177, 2011.
Zhang et al., FGF Ligands of the Postnatal Mammary Stroma Regulate Distinct Aspects of Epithelial Morphogenesis, Stem Cells and Regeneration, 2014, vol. 141, pp. 3352-3362.
Zhang et al., Patient-specific 3D microfluidic tissue model for multiple myeloma, Tissue Engineering Part C: Methods, 2014, pp. 663-670.
Zhou et al., Rapid and efficient generation of transgene-free iPSC from a small volume of cryopreserved blood, Stem Cell Reviews and Reports 11: 652-665. (Year: 2015).
Zilio et al., Universal Hydrophilic Coating of Thermoplastic Polymers Currently Used in Microfluidics, 2014, Biomed. Microdevices, vol. 16(1), pp. 107-114.
Ionescu et al., Compartmental microfluidic system for studying muscle-neuron communication and neuromuscular junction maintenance, 2016 European Journal of Cell Biology, 95:69-88.
DMEM F-12 Formulation, pp. 1-5, 2022.
Mehta et al., The actions of retinoids on cellular growth correlate with their actions on gap junctional communication, JCB 108, 1053-1065, 1989.
Essential 8 medium C037161 Essential8System Brochure (thermofisher.com), downloaded on Aug. 24, 2022, pp. 1-2.

(56) References Cited

OTHER PUBLICATIONS

ISR and WO for PCT/US2021/030128 mailed Aug. 25, 2021, 10 pages.
ISR and WO for PCT/US2021/051492 mailed Dec. 27, 2021, 11 pages.
Lamas et al., Neurotrophic Requirements of Human Motor Neurons Defined Using Amplified and Purified Stem Cell- Derived Cultures, PLosOne, Oct. 22, 2014, vol. 9, No. 10, pp. 1-13.
Li et al., An integrated multi-omic analysis of IPSC-derived motor neurons from C9ORF72 Als patients, iScience, Oct. 12, 2021, vol. 24, No. 11, pp. 1-33.
Kosar et al., A nanofabricated planar aperture as a mimic of the nerve-muscle contact during synaptogenesis, Lab on a Chip, 2016, 6:632-638.
Guo et al., Neuromuscular junction formation between human stem cell-derived motoneurons and human skeletal muscle in a defined system, Biomaterials, 2011 32:9602-9611.
Adams et al., Development of flexible arrays for in vivo neuronal recording and stimulation, Nuclear Instruments & Methods in Physics Research, 2005, 546: 154-159.
Baloh et al., "Transplantation of human neural progenitor cells secreting GDNF into the spinal cord of patients with ALS: a phase 1/2a trial." Nature medicine 28.9 (2022): 1813-1822.
Faravelli et al., "Motor neuron derivation from human embryonic and induced pluripotent stem cells: experimental approaches and clinical perspectives." Stem cell research & therapy 5 (2014): 87.
Klein et al., "GDNF delivery using human neural progenitor cells in a rat model of ALS." Human gene therapy 16.4 (2005): 509-521.
Extended European Search Report in European Patent Application No. 20878850, mailed Dec. 8, 2023 (12 pages).
EPO Communication Article in European Patent Application No. 18802136, mailed Mar. 17, 2023 (10 pages).
Examination Report in Australian Patent Application No. 2017321489, Mailed Mar. 7, 2023 (4 pages).
Sareen et al., Human induced pluripotent stem cells are a novel source of neural progenitor cells (iNPCs) that migrate and integrate in the rodent spinal cord: Human neural progenitor cells, 2014. Journal of Comparative Neurology, vol. 522, No. 12, pp. 2707-2728.
Office Action in Canadian Patent Application No. 3,034,614, mailed Jan. 28, 2025 (3 pages).
Exam Search Report and Written Opinion in Singaporian Patent Application No. 11201901621V, mailed May 12, 2020 (12 pages).
Achyuta A.K.H. et al., A modular approach to create a neurovascular uniton-a-chip. Lab Chip, Sep. 26, 2012, vol. 13, No. 4, pp. 542-553.
EPO Communication in European Patent Application No. 19796470, mailed Jan. 16, 2024 (10 pages).
Klepac et al. "An update on the management of young-onset Parkinson's disease." Degenerative neurological and neuromuscular disease (2013): 53.
Notice of Reasons for Rejection in Japanese Patent Application No. 2020-560894, mailed Apr. 4, 2023 (6 pages).
Wu et al., "Nuclear accumulation of histone deacetylase 4 (HDAC4) exerts neurotoxicity in models of Parkinson's disease." Molecular neurobiology 54 (2017): 6970-6983.
Offica Action in Chinese Patent Application No. 202080074079, mailed Aug. 11, 2023 (11 pages).
Laperle et al., "Human iPSC-derived neural progenitor cells secreting GDNF provide protection in rodent models of ALS and retinal degeneration." Stem cell reports 18.8 (2023): 1629-1642.
Akhtar et al., "Inducible expression of GDNF in transplanted iPSC-derived neural progenitor cells." Stem Cell Reports 10.6 (2018): 1696-1704.
Fernandopulle et al., Transcription factor-mediated differentiation of human iPSCs into neurons, current Protocols in Cell Biology, 2018, 79, e51.
Zhang et al., Molecular biomarkers for embryonic and adult neural stem cell and neurogenesis, BioMed Research International, 2015, vol. 2015, Article ID 727542.
Elis et al., Human IPSC-derived myocardium-on-chip with capillary-like flow for personalized mediine, Biomicrofludics 11, 024105, 2017.
Cardiac cells, Science Direct <https://www.sciencedirect.com/topics/engineerings/cardiac-cell>; 2025.
Romero-Ramos et al., Neural differentiation of stem cells isolated from adult muscle, Journal of Neuroscience Research, 2002, 69:894-907.
PSA (Aniti-anti) Antibiotic-Antimycotic Solutions (100X)-cell culture—TOKU—2 pages downloaded from the internet on Jun. 2, 2025.
Cell Signaling Technology "Certificate of Analysis" for Product No. 9375, Phospho-PKC alpha/beta II (Thr638/641) antibody, Sep. 5, 2019.
Newton, Protein kinase C: structural and spatial regulation by phosphorylation, cofactors, and macromolecular interactions, Chem Rev. Aug. 2001;101(8):2353-64.
Laperle et al., iPSC modeling of young-onset Parkinson's disease reveals a molecular signature of disease and novel therapeutic candidates, Nat Med. Feb. 2020;26(2):289-299.
CA Exam Report for CA 3158428 dated Oct. 8, 2025, 5 pages.
Zhou et al., "The positional identity of iPSC-derived neural progenitor cells along the anterior-posterior axis is controlled in a dosage-dependent manner by bFGF and EGF", Differentiation, 92(4), pp. 183-194, Oct. 2016.
Xu et al., "Effect of leukocyte inhibitory factor on neuron differentiation from human induced pluripotent stem cell- derived neural precursor cells", International Journal of Molecular Medicine, 41(4), pp. 2037-2049, Apr. 2018.
McCaughey-Chapman et al., "Human Cortical Neuron Generation Using Cell Reprogramming: A Review of Recent Advances", Stem Cells and Development, 27(24), pp. 1674-1692, Dec. 2018.
Roberts et al., Fluorescent gene tagging of transcriptionally silent genes in hiPSCs, Stem Cell Reports, 2019, 12:1145-1158.

* cited by examiner f g

Selected flow enriched gene sets
GO_DNA_REPLICATION
GO_ORGAN_REGENERATION
GO_DNA_REPAIR
GO_ENDODERMAL_CELL_DIFFERENTIATION
GO_ORGANELLE_FISSION
GO_COLLAGEN_FIBRIL_ORGANIZATION
GO_RESPONSE_TO_TYPE_I_INTERFERON
GO_POSITIVE_REGULATION_OF_PHAGOCYTOSIS
GO_VASCULATURE_DEVELOPMENT
(FWER P-val = 0.001 - Max)

FIG. 2 d

| Upregulated in PC3 (ALS Axis) | SIZE | RNA FDR | SIZE | Prot FDR |
|---|---|---|---|---|
| KEGG_REGULATION_OF_ACTIN_CYTOSKELETON | 197 | 0.0079 | 51 | 0.0104 |
| KEGG_FOCAL_ADHESION | 192 | 0.0160 | 34 | 0.0114 |
| KEGG_AMYOTROPHIC_LATERAL_SCLEROSIS_ALS | 51 | 0.0097 | 19 | 0.0370 |
| KEGG_CELL_CYCLE | 121 | 0.0000 | 20 | 0.7014 |
| KEGG_P53_SIGNALING_PATHWAY | 66 | 0.0000 | | NA |
| KEGG_ECM_RECEPTOR_INTERACTION | 82 | 0.0000 | | NA |

| Downregulated in PC3 (ALS Axis) | SIZE | RNA FDR | SIZE | Prot FDR |
|---|---|---|---|---|
| KEGG_SPLICEOSOME | 59 | 0.8965 | 66 | 0.0000 |
| KEGG_OXIDATIVE_PHOSPHORYLATION | 63 | 0.0000 | 63 | 0.0000 |
| KEGG_HUNTINGTONS_DISEASE | 75 | 0.0013 | 75 | 0.0013 |
| KEGG_PARKINSONS_DISEASE | 63 | 0.0110 | 63 | 0.0110 |
| KEGG_RIBOSOME | 86 | 0.0258 | 59 | 0.8965 |
| KEGG_MATURITY_ONSET_DIABETES_OF_THE_YOUNG | 19 | 0.0040 | NA | NA |
| KEGG_OLFACTORY_TRANSDUCTION | 105 | 0.0214 | NA | NA |

e

C

FIG. 4 d Protein Meta-analysis

| SYMBOL | log2FC | FDR | log_odds |
|---|---|---|---|
| VIME | 0.515 | 0 | 601.8655 |
| SERPH | 0.422 | 0 | 395.7125 |
| DDC | 0.913 | 0 | 334.7045 |
| TAGL2 | 0.6 | 0 | 213.826 |
| ITAV | 0.441 | 0 | 151.011 |
| ITA6 | 0.415 | 0 | 122.7577 |
| PERI | 0.894 | 0 | 111.5347 |
| EZRI | 0.368 | 0 | 109.5264 |
| ITB1 | 0.367 | 0 | 97.08725 |
| NEUG | 1.393 | 0 | 77.63305 |
| KS6A3 | 0.397 | 0 | 61.84465 |
| CALD1 | 0.499 | 0 | 44.4653 |

| SYMBOL | log2FC | FDR | log_odds |
|---|---|---|---|
| SERC | -0.3529 | 0 | 115.427 |
| ZN512 | -0.3635 | 0 | 140.23 |
| PSIP1 | -0.3747 | 0 | 155.765 |
| HDGR3 | -0.3816 | 0 | 99.292 |
| HMGB3 | -0.391 | 0 | 91.4217 |
| H4 | -0.3958 | 0 | 204.581 |
| PEA15 | -0.4082 | 0 | 69.3132 |
| ALDOC | -0.4111 | 0 | 70.9487 |
| HMGA1 | -0.4511 | 0 | 43.7968 |
| COTL1 | -0.4623 | 0 | 246.636 |
| ELAV2 | -0.5046 | 0 | 90.7544 |
| NOVA1 | -0.5271 | 0 | 281.868 |
| ALBU | -0.7349 | 0 | 100.582 |
| H10 | -0.7558 | 0 | 119.552 |
| RABP1 | -0.8319 | 0 | 257.412 |
| FABP7 | -1.6567 | 0 | 167.279 |

FIG. 5

C

| Enriched in Static Condition | FWER p- |
|---|---|
| GO_SYNAPTIC_SIGNALING | 0 |
| GO_REGULATION_OF_NEUROTRANSMITTER_LEVELS | 0 |
| GO_NEUROTRANSMITTER_TRANSPORT | 0 |
| GO_PRESYNAPTIC_PROCESS_INVOLVED_IN_ | 0 |
| GO_REGULATION_OF_AMINE_TRANSPORT | 0 |
| GO_MODULATION_OF_SYNAPTIC_TRANSMISSION | 0 |
| GO_NEURON_RECOGNITION | 0 |
| GO_GLUTAMATE_RECEPTOR_SIGNALING_PATHWAY | 0 |
| GO_REGULATION_OF_CALCIUM_ION_DEPENI | 0 |
| GO_REGULATION_OF_INSULIN_SECRETION_I | 0 |
| GO_POSITIVE_REGULATION_OF_SYNAPSE_ASSE | [illegible] |
| GO_REGULATION_OF_SYNAPSE_STRUCTURE | 0.001 |
| GO_MEMBRANE_DEPOLARIZATION | 0.001 |
| GO_GLUTAMATE_SECRETION | 0.001 |

d e

FIG. 6 f

| | | | | |
|---|---|---|---|---|
| REACTOME_3_UTR_MEDIATED_TRANSLATIONAL_REGULATION | 105 | 0.00001 | 66 | -1.00001 |
| REACTOME_S_PHASE | 105 | 0.00001 | 35 | -1.00001 |
| KEGG_RIBOSOME | 86 | 0.00001 | 61 | -0.437247 |
| GO_ENDOPLASMIC_RETICULUM_LUMEN | 174 | 0.001352 | 44 | 0.00001 |
| GO_EXTRACELLULAR_STRUCTURE_ORGANIZATION | 262 | 0.000418 | 44 | 0.0093874 |
| GO_ANCHORING_JUNCTION | 457 | 0.00065 | 198 | 0.0159378 |
| GO_CELL_SUBSTRATE_JUNCTION | 379 | 0.00001 | 176 | 0.0211517 |
| GO_FORMATION_OF_PRIMARY_GERM_LAYER | 100 | 0.001381 | 17 | 0.0262797 |
| GO_PIGMENT_GRANULE | 100 | 0.00001 | 57 | 0.0328575 |
| KEGG_ECM_RECEPTOR_INTERACTION | 82 | 0.012805 | 17 | 0.0238621 |
| GO_CELL_JUNCTION_ASSEMBLY | 119 | 0.014385 | 32 | 0.0234495 |
| GO_HOMOTYPIC_CELL_CELL_ADHESION | 42 | 0.005955 | 16 | 0.0321827 |
| GO_INTERMEDIATE_FILAMENT | 59 | 0.014856 | 23 | 0.0242723 |
| GO_POSITIVE_REGULATION_OF_RESPONSE_TO_EXTERNAL_STIMULUS | 222 | 0.040873 | 24 | 0.0010862 |
| GO_CELL_JUNCTION_ORGANIZATION | 169 | 0.03803 | 46 | 0.0077758 |
| GO_UROGENITAL_SYSTEM_DEVELOPMENT | 270 | 0.020193 | 33 | 0.0274091 |
| KEGG_FOCAL_ADHESION | 190 | 0.041186 | 42 | 0.0068984 |
| GO_POSITIVE_REGULATION_OF_LOCOMOTION | 348 | 0.030204 | 49 | 0.0231768 |
| GO_PLASMA_MEMBRANE_ORGANIZATION | 190 | 0.027399 | 41 | 0.0343642 |
| GO_CYTOPLASMIC_REGION | 253 | 0.033778 | 78 | 0.0392647 |
| GO_PROTEIN_N_LINKED_GLYCOSYLATION | 73 | 0.043326 | 16 | 0.0392297 |
| AR_ENDOTHELIAL_GROWTH_FACTOR_RECEPTOR_SIGNALING_PATHWAY | 69 | 0.207483 | 16 | 0.0069015 |
| GO_INTEGRIN_MEDIATED_SIGNALING_PATHWAY | 74 | 0.131155 | 15 | 0.0076377 |
| GO_PLATELET_ACTIVATION | 119 | 0.142011 | 27 | 0.0226581 |
| GO_CELL_MATRIX_ADHESION | 108 | 0.177916 | 20 | 0.0238239 |
| REACTOME_CELL_CELL_COMMUNICATION | 105 | 0.383815 | 27 | 0.024241 |
| GO_CELL_ACTIVATION | 445 | 0.207255 | 66 | 0.0245216 |
| GO_LEUKOCYTE_MIGRATION | 193 | 0.193708 | 42 | 0.0255654 |
| GO_SARCOLEMMA | 119 | 0.089805 | 30 | 0.0332141 |
| GO_LIPOSACCHARIDE_METABOLIC_PROCESS | 97 | 0.075577 | 23 | 0.0341353 |
| GO_CONTRACTILE_FIBER | 184 | 0.197655 | 47 | 0.0341942 |
| GO_INTERMEDIATE_FILAMENT_CYTOSKELETON | 97 | 0.156579 | 31 | 0.0404996 |
| GO_PROTEIN_SECRETION | 95 | 0.178324 | 21 | 0.04066 |
| GO_LEUKOCYTE_ACTIVATION | 323 | 0.495366 | 38 | 0.0406919 |
| GO_REGULATION_OF_CALCIUM_ION_TRANSMEMBRANE_TRANSPORT | 96 | -1.00001 | 17 | 0.041291 |
| KEGG_AMYOTROPHIC_LATERAL_SCLEROSIS_ALS | 50 | 0.086795 | 15 | 0.0415261 |
| GO_INNER_MITOCHONDRIAL_MEMBRANE_PROTEIN_COMPLEX | 76 | 0.00001 | 48 | -0.00001 |
| KEGG_PARKINSONS_DISEASE | 93 | 0.000104 | 57 | -0.00109 |
| KEGG_PROTEASOME | 40 | 0.000107 | 20 | -0.996369 |
| GO_OXIDATIVE_PHOSPHORYLATION | 76 | 0.000189 | 51 | -0.00001 |
| GO_INNER_MITOCHONDRIAL_MEMBRANE_PROTEIN_COMPLEX | 76 | 0.00001 | 48 | -0.00001 |
| GO_RESPIRATORY_CHAIN | 73 | 0.000184 | 49 | -0.00001 |
| GO_OXIDATIVE_PHOSPHORYLATION | 76 | 0.000189 | 51 | -0.00001 |
| REACTOME_RESPIRATORY_ELECTRON_TRANSPORT | 64 | 0.000192 | 47 | -0.00001 |
| GO_NADH_DEHYROGENASE_COMPLEX | 42 | 0.000214 | 33 | -0.00001 |
| OTIC_COUPLING_AND_HEAT_PRODUCTION_BY_UNCOUPLING_PROTEINS | 67 | 0.000431 | 47 | -0.00001 |
| REACTOME_TCA_CYCLE_AND_RESPIRATORY_ELECTRON_TRANSPORT | 103 | 0.002348 | 67 | -0.00001 |
| GO_MITOCHONDRIAL_RESPIRATORY_CHAIN_COMPLEX_I_BIOGENESIS | 51 | 0.005296 | 34 | -0.00001 |
| GO_MITOCHONDRIAL_RESPIRATORY_CHAIN_COMPLEX_ASSEMBLY | 63 | 0.01272 | 38 | -0.00001 |
| GO_MITOCHONDRIAL_MEMBRANE_PART | 132 | 0.013737 | 66 | -0.00001 |
| KEGG_HUNTINGTONS_DISEASE | 153 | 0.048231 | 65 | -6.41E-05 |
| KEGG_PARKINSONS_DISEASE | | 0.000104 | | -0.00109 |
| KEGG_ALZHEIMERS_DISEASE | | 0.009772 | | -0.001684 |
| GO_DNA_PACKAGING | | 0.093578 | | -0.005705 |
| KEGG_OXIDATIVE_PHOPHORYLATION | 95 | 0.017408 | 57 | -6.77E-05 |
| GO_POSITIVE_REGULATION_OF_SYNAPSE_ASSEMBLY | | -0.00001 | | NA |
| REACTOME_OLFACTORY_SIGNALING_PATHWAY | | -0.00067 | | NA |
| GO_PRESYNAPTIC_ACTIVE_ZONE | | -0.00805 | | NA |
| GO_REGULATION_OF_SYNAPSE_ASSEMBLY | | -0.01272 | | NA |
| KEGG_OLFACTORY_TRANSDUCTION | | -0.01524 | | NA |
| GO_SENSORY_PERCEPTION_OF_CHEMICAL_STIMULUS | | -0.01798 | | NA |
| GO_REGULATION_OF_SYNAPSE_ORGANIZATION | | -0.02391 | | NA |
| GO_PROTEIN_LOCALIZATION_TO_SYNAPSE | | -0.02398 | | NA |
| GO_GLUTAMATE_RECEPTOR_SIGNALING_PATHWAY | | -0.02459 | | NA |
| GO_BICARBONATE_TRANSPORT | | -0.02476 | | NA |
| GO_CEREBELLAR_CORTEX_FORMATION | | -0.0251 | | NA |
| GO_MAIN_AXON | | -0.04388 | | 0.8697206 |
| KEGG_SLICEOSOME | 123 | 0.216716 | 58 | -0.00001 |
| REACTOME_TRANSCRIPTION | 136 | 0.978553 | 32 | -0.00001 |
| GO_MRNA_PROCESSING | 395 | -1.00001 | 133 | -0.00001 |
| GO_RNA_SPLICING | 340 | -1.00001 | 125 | -0.00001 |

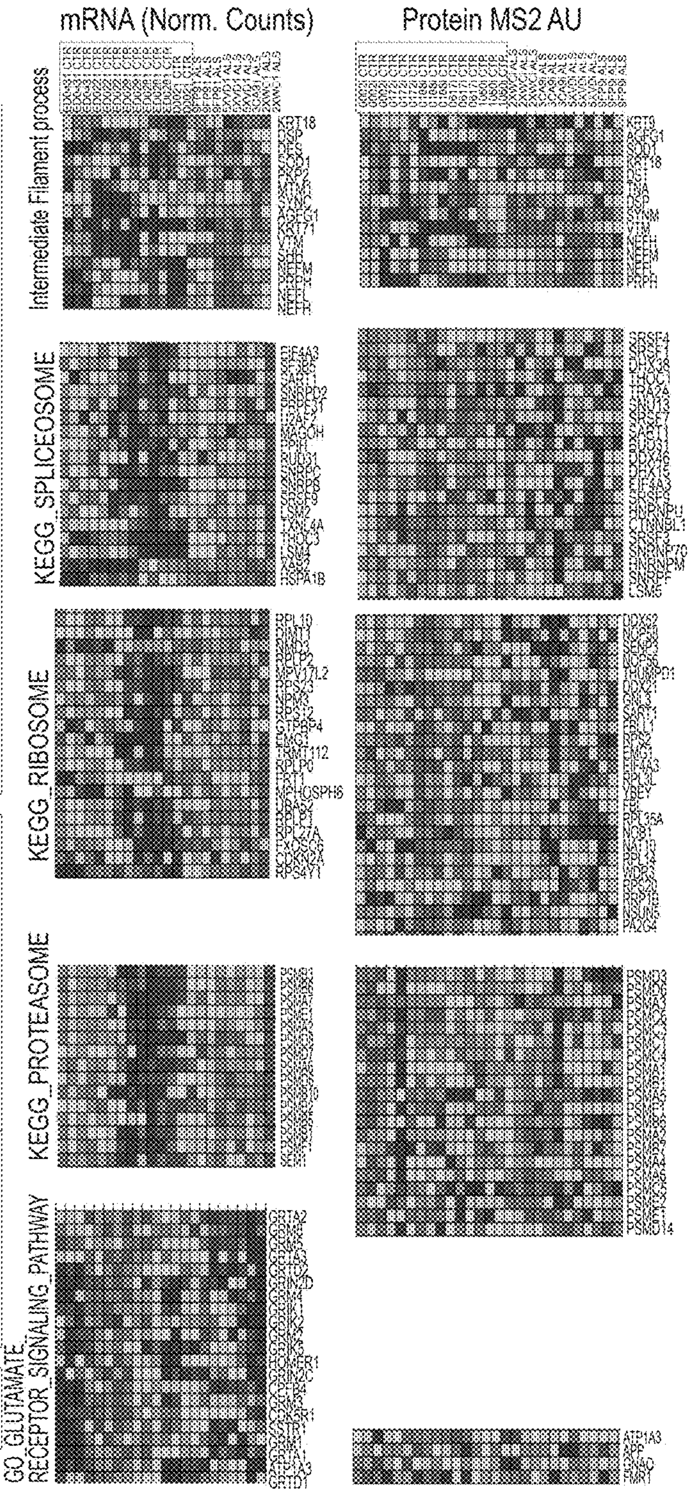

COMPLEX MICROFLUIDIC MODELS FOR ALS INCLUDING NF BIOMARKERS FOR ALS RESEARCH AND DRUG DEVELOPMENT

CROSS-REFERENCE TO RELATED APPLICATIONS

This application is a national phase of International Application No. PCT/US2021/051492, filed Sep. 22, 2021, which designated the U.S. and that International Application was published under PCT Article 21(2) in English. This application includes a claim of priority under 35 U.S.C. § 119(e) to U.S. provisional patent application No. 63/081,507, filed Sep. 22, 2020, the entirety of which is hereby incorporated by reference.

STATEMENT REGARDING FEDERALLY SPONSORED RESEARCH OR DEVELOPMENT

This invention was made with Government support under Grant No. NS105703 awarded by National Institutes of Health. The Government has certain rights in the invention.

FIELD OF INVENTION

This invention relates to devices and processes to identify new drug targets and pathogenesis of amyotrophic lateral sclerosis (ALS), to identify drugs to treat ALS and to the treatment of ALS.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Currently, there is no treatment for ALS and animal models lack diversity/fidelity of human disease. Thus, there remains a need in the art for system and models for identification of new drug targets and pathogenesis of ALS, and to identify drugs to treat ALS.

Motor neuron disease (MND), also known as ALS or Lou Gehrig's disease is a terminal condition characterized by progressive motor neuron loss that causes death within 2-5 years of diagnosis on average. Approximately 10% of cases are hereditary (known as familial ALS), caused by monogenetic mutations in genes inherited in an autosomal-dominant manner. The remaining 90% of cases are idiopathic, also known as sporadic, with no clear etiology. Two drugs (riluzole and edaravone) show modest slowing of disease progression, however the common mechanisms by which ALS originates and genetic and environmental factors that augment disease progression rates remain unclear.

Neuronal intermediate filaments (IFs) have long been associated with neuropathology of both familial and sporadic ALS. Classical pathological descriptions of ALS patient spinal cords include characteristic ubiquinated perikaryal hyaline inclusions in spinal motor neurons consisting of intermediate neurofilaments light (NFL), medium (NFM) and heavy (NFH), and peripherin. Neurofilament low (NFL), medium (NFM), and high (NFH) and peripherin (PERI) immunoreactive protein entanglements are also found in swollen proximal axons, known as spheroids, and are associated with lysosomal inclusions known as Bunina bodies. Analysis of patient blood, cerebral spinal fluid, urine and other electrophysiological tests have identified ALS specifying biomarkers including neurofilaments in patient cerebrospinal fluid (CSF). However, despite their predominance, the role of neuronal IFs in the pathogenesis of ALS is unknown.

Murine and human induced pluripotent stem cell derived in vitro models of familial ALS are utilized to seek disease mechanisms that may translate to better understanding and treatments of ALS. Super oxide dismutase 1 (SOD1) mutant animals and induced pluripotent stem cell (iPSC) derived motor neurons (MNs) in vitro exhibit motor neuron cell death similar to SOD-1 ALS patients. However, consensus on the cause of ALS from these mutations remains unknown and may not represent the majority of patients that do not have monogenetic origin.

Microphysiological systems (MPS), also known as tissue chips, incorporate induced pluripotent stem cell derived tissues in microeningeered three dimensional compartments that enable the co-culture of different cell types to enable enhanced reproduction of human physiology in vitro. A defining characteristic of these systems is the ability to perfuse media in microfluidic channels over time, which has been shown to be critical for the development of gut, and lung tissues. By incorporating media perfusion through a brain vasculature compartment that can interact with nervous tissue, investigators have utilized MPS to study human blood brain barrier (BBB) dynamics and barrier pathophysiology in vitro. We previously characterized a spinal cord tissue chip model that promoted the maturation of iPSC-derived motor neuron cultures in static conditions.

Accordingly, there remains a need in the art for systems to model ALS which allow drug screening and development as well as further study to understand the pathophysiology of ALS.

SUMMARY OF THE INVENTION

The following embodiments and aspects thereof are described and illustrated in conjunction with compositions and methods which are meant to be exemplary and illustrative, not limiting in scope.

Described herein is a method of identifying an agent of interest, comprising: contacting a quantity of neurons or a quantity of ventralized spinal motor neuron progenitor cells (spNPCs) with a test agent; measuring one or more parameters relating to the quantity of neurons or the quantity of ventralized spNPCs; and identifying the test agent as the agent of interest if the test agent modulates the one or more parameters, wherein the quantity of neurons or the quantity of spNPCs is differentiated from induced pluripotent stem cells (iPSCs).

In other embodiments, the quantity of neurons or the quantity of spNPCs can be in a top channel of a multi-channel 3-dimenional (3-D) cell culture chip. In other embodiments, the method can further comprise adding brain microvascular cells (BMECs) to a bottom channel of the multi-channel 3-D cell culture chip. In other embodiments, the method can further comprise adding culture media to a bottom channel of the multi-channel 3-D cell culture chip.

In other embodiments, the culture media can be continuously perfused through the bottom channel of the multi-channel 3-D cell culture chip.

In other embodiments, the neurons can be spinal motor neurons.

In other embodiments, the iPSCs can be from amyotrophic lateral sclerosis (ALS) patients.

In other embodiments, the agent of interest can be a drug for treating amyotrophic lateral sclerosis (ALS). In other embodiments, the agent of interest can be a drug for treating young onset amyotrophic lateral sclerosis (YOALS). In other embodiments, the agent of interest can be a drug that can cross the blood-brain barrier.

In other embodiments, the one or more parameters can be expression level of one or more genes or one or more proteins, and the test agent can be identified as the agent of interest if the test agent increases or decreases the expression level of one or more genes as compared to a reference level for each gene, or the test agent increases or decreases the expression level of one or more proteins as compared to a reference level for each protein.

In other embodiments, the one or more genes can be selected from the group consisting of TOMM40L, BAX, RAC1, BAD, DAXX, PRP2, GPX1, SOD1, PP3R2, CAT, MAP2K6, TNFRSF1A, NEFM, PRPH, NEFL, NEFH, and combinations thereof, and the test agent can be identified as the agent of interest if the test agent increases or decreases the expression level of the one or more genes as compared to a reference level for each gene.

In other embodiments, the one or more genes can be selected from the group consisting of neurofilament light (NEFL), neurofilament medium (NEFM), neurofilament heavy (NEFH), peripherin (PRPH), neuronal microtubule gene beta 3 tubulin (TUBB3), and combinations thereof, and the test agent can be identified as the agent of interest if the test agent increases or decreases the expression level of the one or more genes as compared to a reference level for each gene.

In other embodiments, the one or more genes can be neurofilament light (NEFL), neurofilament medium (NEFM), neurofilament heavy (NEFH), and peripherin (PRPH), and the test agent can be identified as the agent of interest if the test agent increases or decreases the expression level of the one or more genes as compared to a reference level for each gene.

In other embodiments, the one or more proteins can be selected from the group consisting of CCS, SLS1A2, PPP2CB, BCL2L1, RAC1, PPP3R1, SOD1, TOMM40, GPX1, CAT, MAPK14, NEFH, NEFM, NEFL, PRPH, and combinations thereof, and the test agent can be identified as the agent of interest if the test agent increases or decreases the expression level of one or more proteins as compared to a reference level for each protein. In other embodiments, the one or more proteins can be selected from the group consisting of neurofilament light (NFL), neurofilament medium (NFM), neurofilament heavy (NFH), peripherin (PERI), neuronal microtubule gene beta 3 tubulin (TBB3) protein, and combinations thereof, and the test agent can be identified as the agent of interest if the test agent increases or decreases the expression level of one or more proteins as compared to a reference level for each protein. In other embodiments, the one or more proteins can be neurofilament light (NFL), neurofilament medium (NFM), neurofilament heavy (NFH), and peripherin (PERI), and the test agent can be identified as the agent of interest if the test agent increases or decreases the expression level of one or more proteins as compared to a reference level for each protein.

Further described herein is a system, comprising: a multi-channel 3-dimenional cell culture chip; a quantity of neurons or a quantity of ventralized spinal motor neuron progenitor cells (spNPCs); and cell culture media.

In other embodiments, the neurons can be spinal motor neurons.

In other embodiments, the cell culture media can be continuously perfused through the multi-channel 3-dimenional cell culture chip.

In other embodiments, the system can further comprise a test agent.

In other embodiments, the quantity of neurons or the quantity of spNPCs can be differentiated from induced pluripotent stem cells (iPSCs).

In other embodiments, the iPSCs can be from amyotrophic lateral sclerosis (ALS) patients.

Further described herein is a method of generating spinal motor neurons for an amyotrophic lateral sclerosis (ALS) model, comprising: coating a top channel of a multi-channel 3-dimenional (3D) cell culture chip with substrate for culturing cells; coating a bottom channel of the multi-channel 3D cell culture chip with a mixture comprising collagen IV, fibronectin, and water; seeding the top channel with ventralized spinal motor neuron progenitor cells (spNPCs), wherein the ventralized spNPCs are in a media comprising IMDM/F12, B27, N2, NEAA, ascorbic acid, retinoic acid, cAMP, SAG, glial cell line-derived neutrotrophic factor, brain derived neutrotrophic factor, penicillin-streptavidin (PSA), and Y-27632; and culturing the ventralized spNPCs to differentiate them into spinal motor neurons.

In other embodiments, the media can comprise IMDM/F12, B27, N2, about 1% NEAA, about 200 ng/ml ascorbic acid, about 0.5 μM retinoic acid, about 0.1 μM cAMP, about 0.1 μM SAG, about 10 ng/ml glial cell line-derived neutrotrophic factor, about 10 ng/ml brain derived neutrotrophic factor, about 1% penicillin-streptavidin (PSA), and 10 μM Y-27632.

In other embodiments, the method can further comprise flushing excess cells with the media without the Y-27632 after about 2 hours of incubation.

In other embodiments, culturing the ventralized spNPCs to differentiate them into spinal motor neurons can comprise continuously perfusing the media through the top or the bottom channel to differentiate the ventralized spNPCs into spinal motor neurons.

In other embodiments, the substrate for culturing cells can be MATRIGEL matrix.

In other embodiments, the ventralized spNPCs can be differentiated from induced pluripotent stem cells (iPSCs).

In other embodiments, the ventralized spNPCs can be differentiated from iPSCs from ALS patients.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

Phase contrast images of chips under static and flow conditions. (c) Representative confocal reconstruction of Phosphorylated Neurofilament heavy chain epitope 32 (SMI32) and MKi67 immunostaining of whole chips from static (top) and flow (bottom) conditions. (d) MKi67 staining quantification and thickness measurements. (e) Maximum projection confocal image of tissue chip section stained with SMI32 and motor neuron (when co-expressed with SMI32) and BMEC marker Islet-1 (ISL1). (f) Principal component analysis (PCA) analysis of mRNA transcripts quantified from whole neural (top) channel extracts. (g) boxplot of MKi67 mRNA counts. Gene set enrichment pathways generated from PC1 geneloading, ranked by family-wise error rate (FWER) p-value. (h) Unsupervised clustering heatmap of top 20 differentially expressed genes between flow vs static conditions determined by differential expression analysis. Cells colored by row Z-score. (i) Boxplots of mRNA counts of vascular related genes. Stars denote p-values by *p<0.05, p<0.01, *p<0.001, ****p<0.0001. Box middle line denotes mean, hinges denote 25% and 75% interquartile range, whisker denotes data within a multiple of 1.5× interquartile range.

Figure 2:
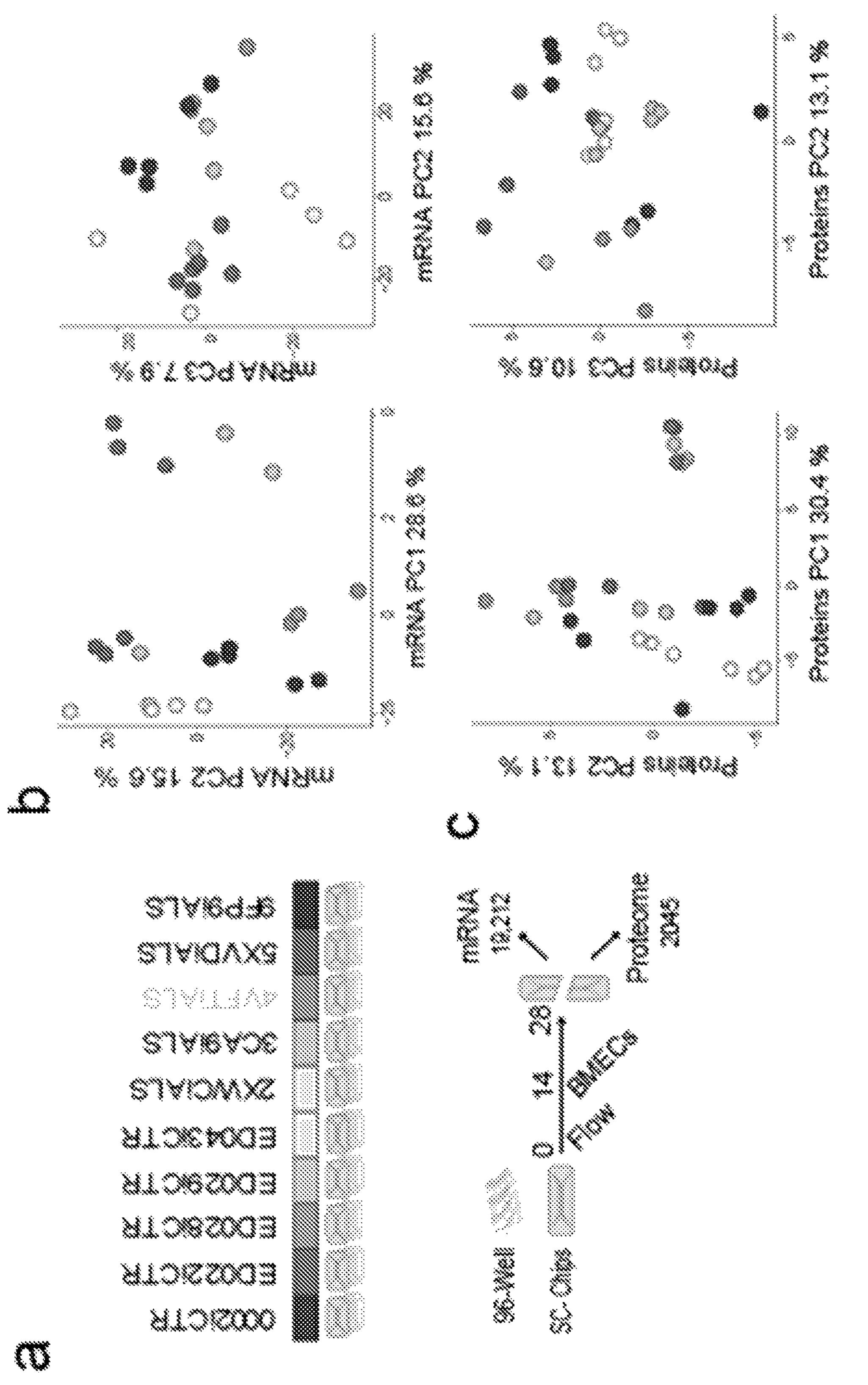

FIG. 2, panels a-d, depicts altered cellular pathways in sporadic ALS patient SC-Chips contribute to ALS-specific signatures. (a) Color key of patient lines and experimental setup of ALS signature discovery studies. Chips and 96 well plate seeded in parallel. 02iCTR BMECs seeded in all chips at day 14. (b,c) PCA analyses of mRNA-Seq (b) and proteomic (c) data from split chips cultured for 28 days. Colored dots represent one chip replicate and match patient color key (d) Gene set enrichment pathways of PC3 geneloading ranked by false discovery rate (FDR) p-value of protein data. Size denotes number of genes used in each gene set term for each dataset.

Figure 3:
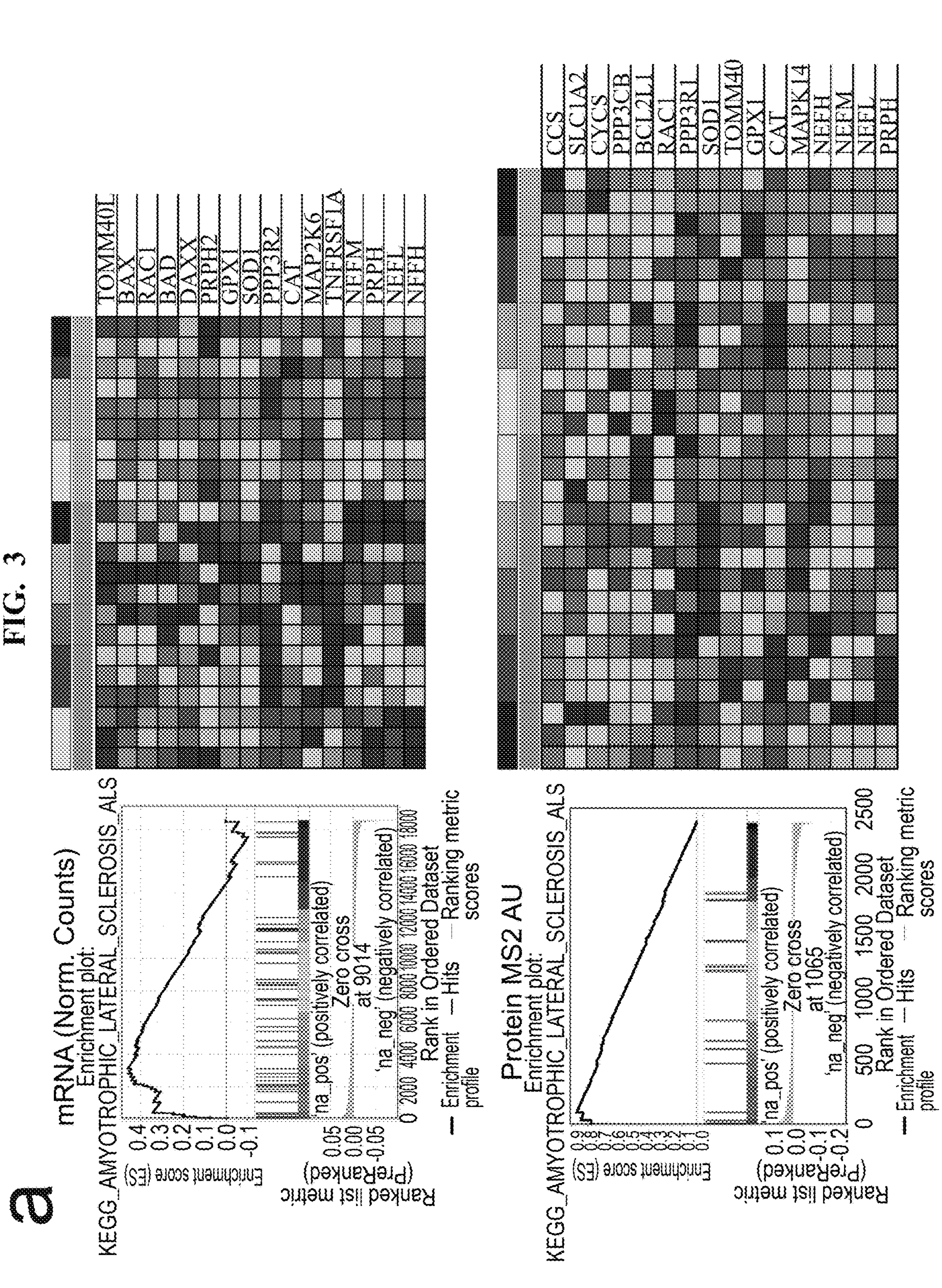
Figure 3:
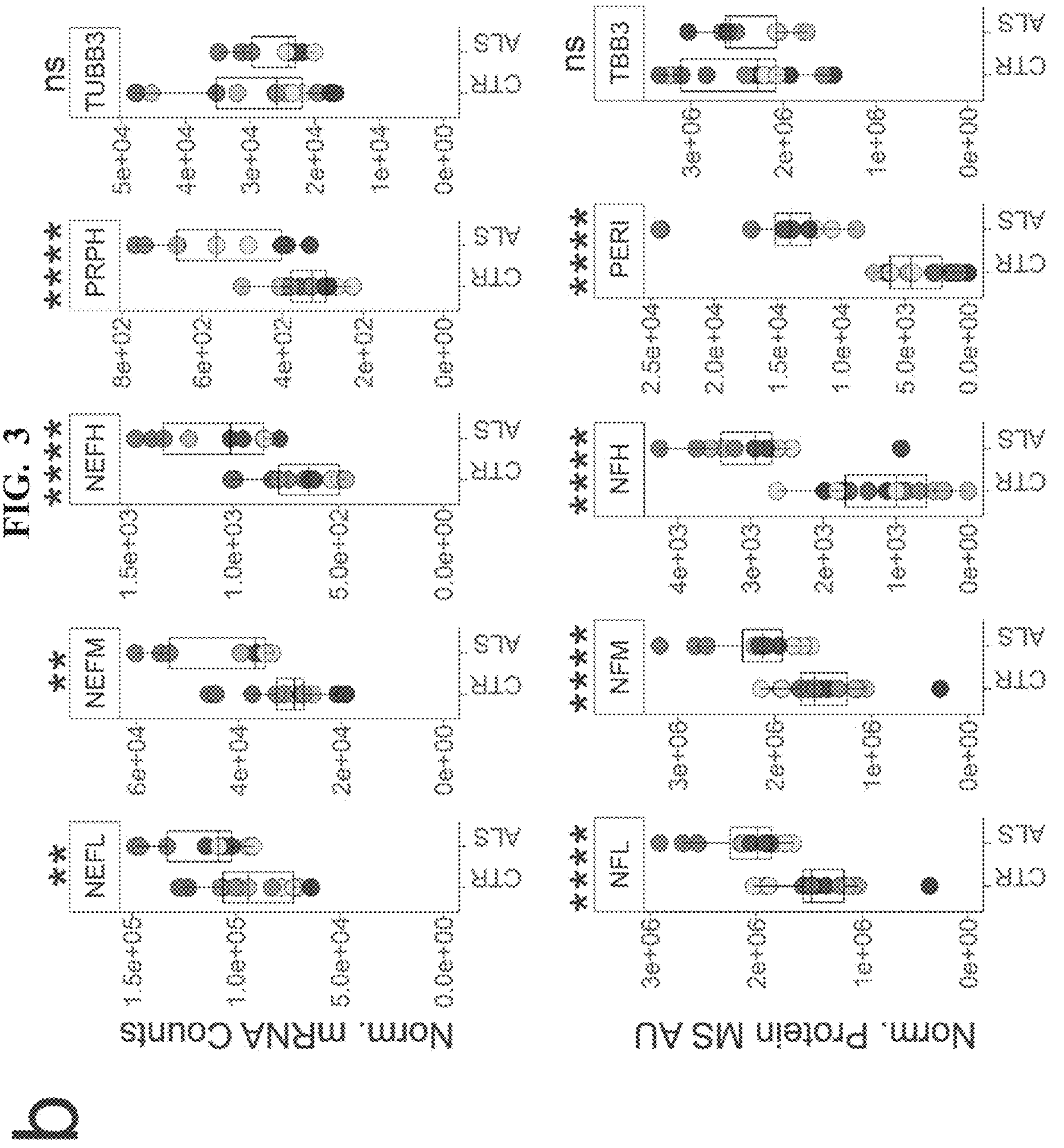
Figure 3:
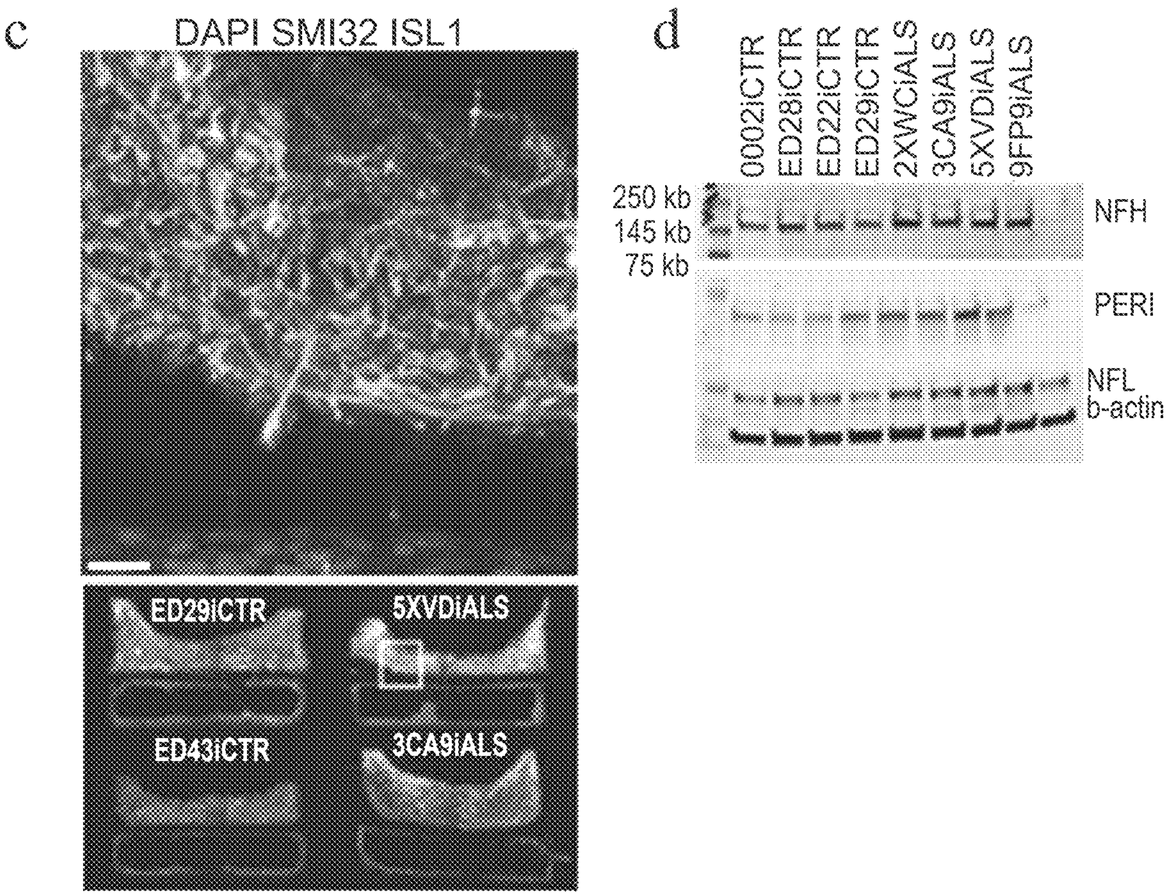
Figure 3:
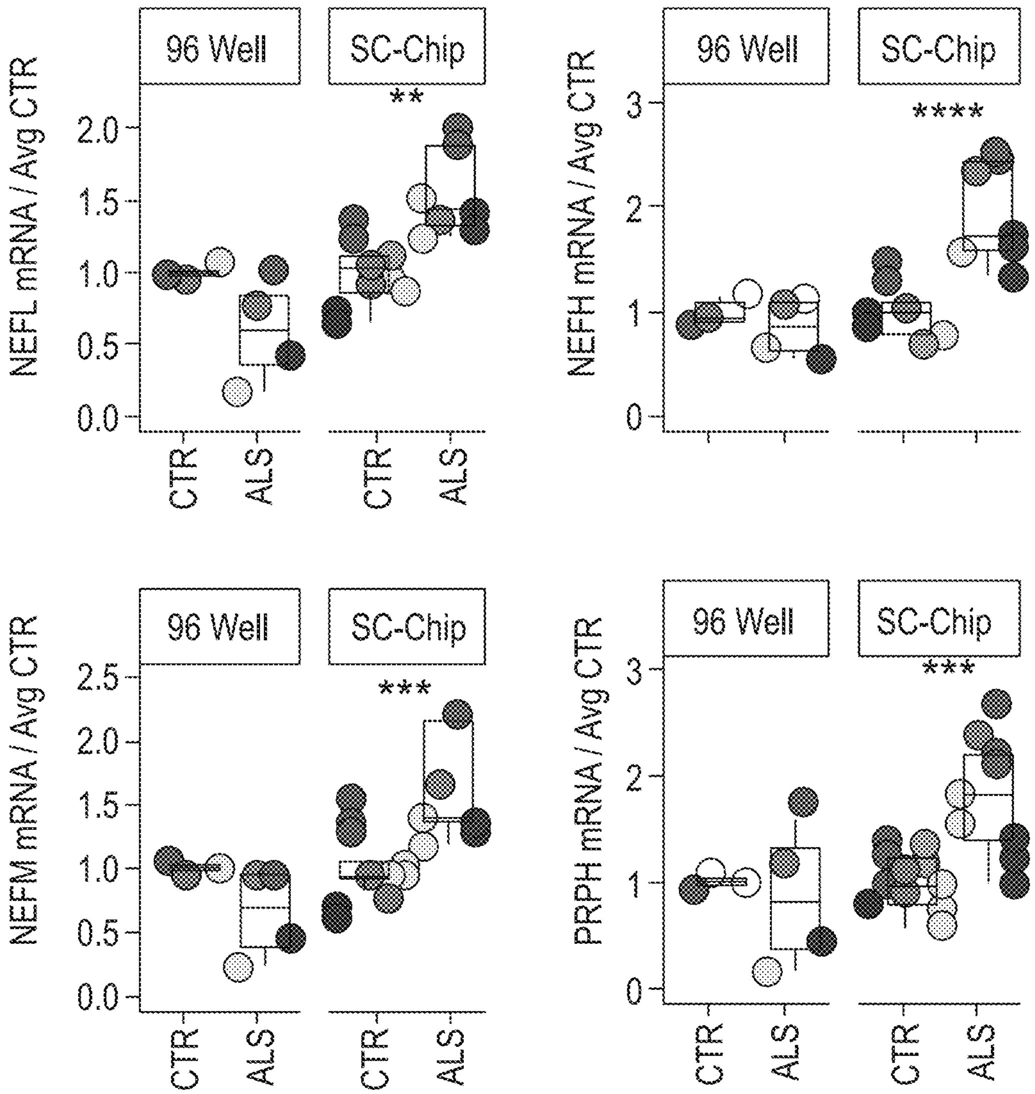

FIG. 3, panels a-e, depicts young onset ALS (YOALS) patient chips contain increased neurofilament expression. (a) Enrichment plots and heatmaps of top 16 genes in KEGG_AMYOTROPHIC_LATERAL_SCLEROSIS_ALS gene set ranked by enrichment score. Cells colored by row Z-score. (b) Boxplots of gene transcript expression (top) of neurofilament light (NEFL), medium (NEFM) and heavy (NEFH), peripherin (PRPH) and neuronal microtubule gene beta 3 tubulin (TUBB3). Protein expression in mass spec arbitrary units (MS AU) (bottom) of neurofilament light (NFL), medium (NFM) and heavy (NFH), peripherin (PERI) and neuronal microtubule gene beta 3 tubulin (TBB3) protein. Significance calculated by p-corrected Wald's test for mRNA and false discovery rate (FDR) for protein. Stars denote p-values by *p<0.05p<0.01, *p<0.001, ****p<0.0001. (c) Representative confocal images of 100 um tissue chip sections immunostained with 4',6-diamidino-2-phenylindole (DAPI), neurofilament epitope 32 (SMI32) and motor neuron transcription factor ISL1 at 10× (bottom) and close-up of 5XVDiALS chip neurons (white box) shown in 3D at slight downward angle (top). (d) Western blot and quantification of neurofilament heavy chain (NFH), neurofilament light chain (NFL), and peripherin (PERI). Quantification normalized for loading by beta-actin. (e) Boxplots of mRNA expression of neurofilament genes in parallel cultures from 96 well plate (96W) and chips. Box middle line denotes mean, hinges denote 25% and 75% interquartile range, whisker denotes data within a multiple of 1.5× interquartile range.

Figure 4:
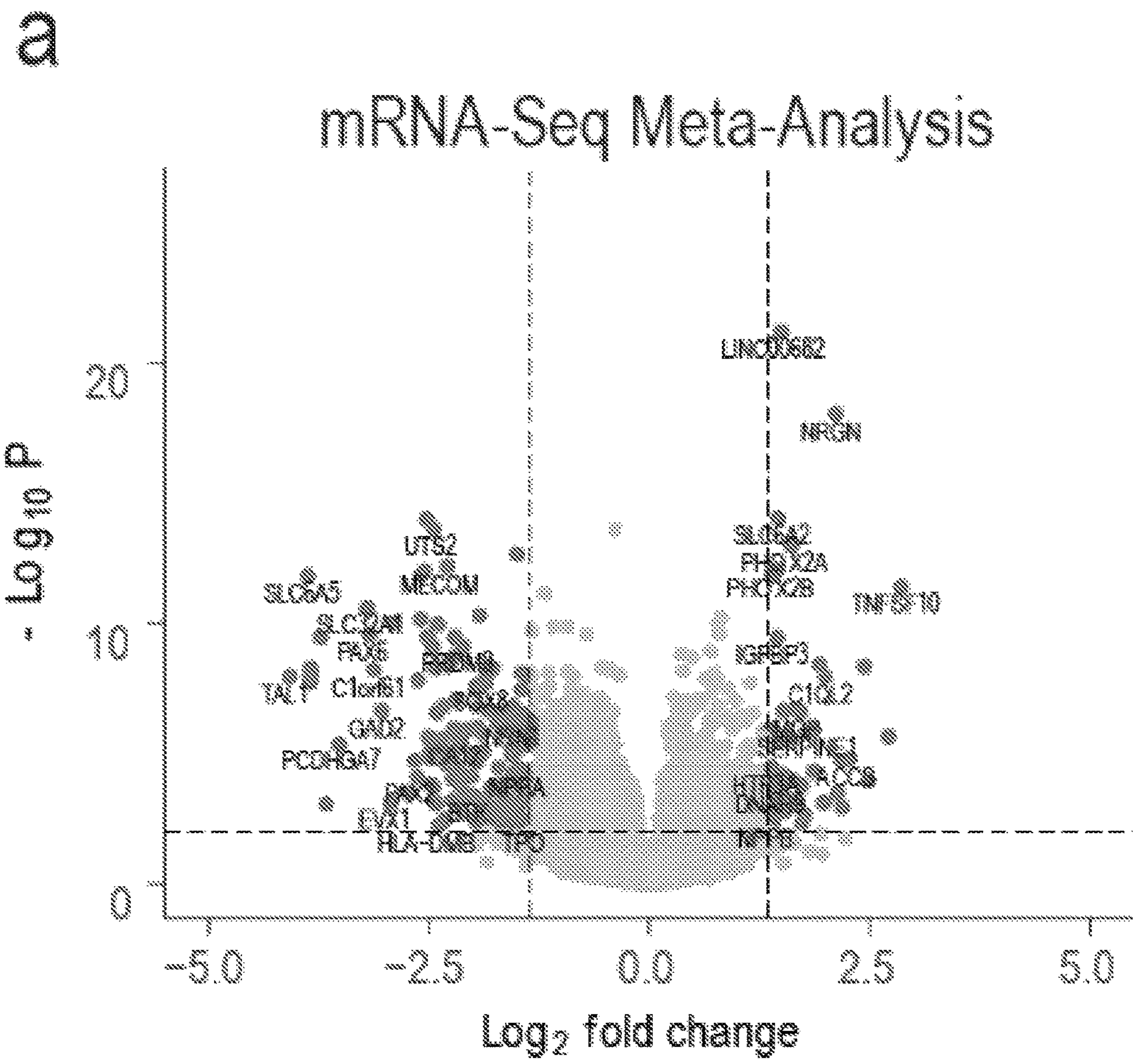
Figure 4:
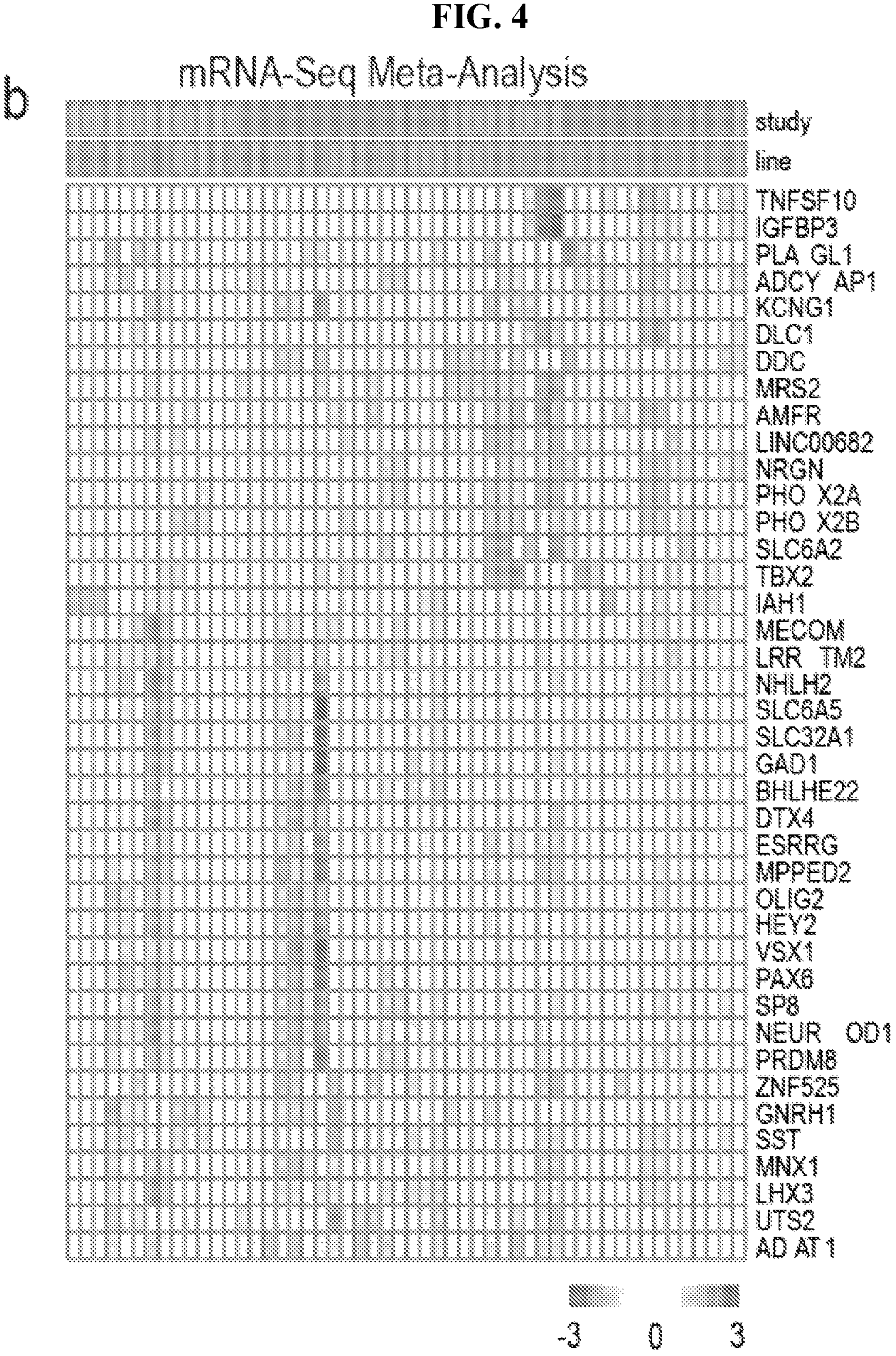
Figure 4:
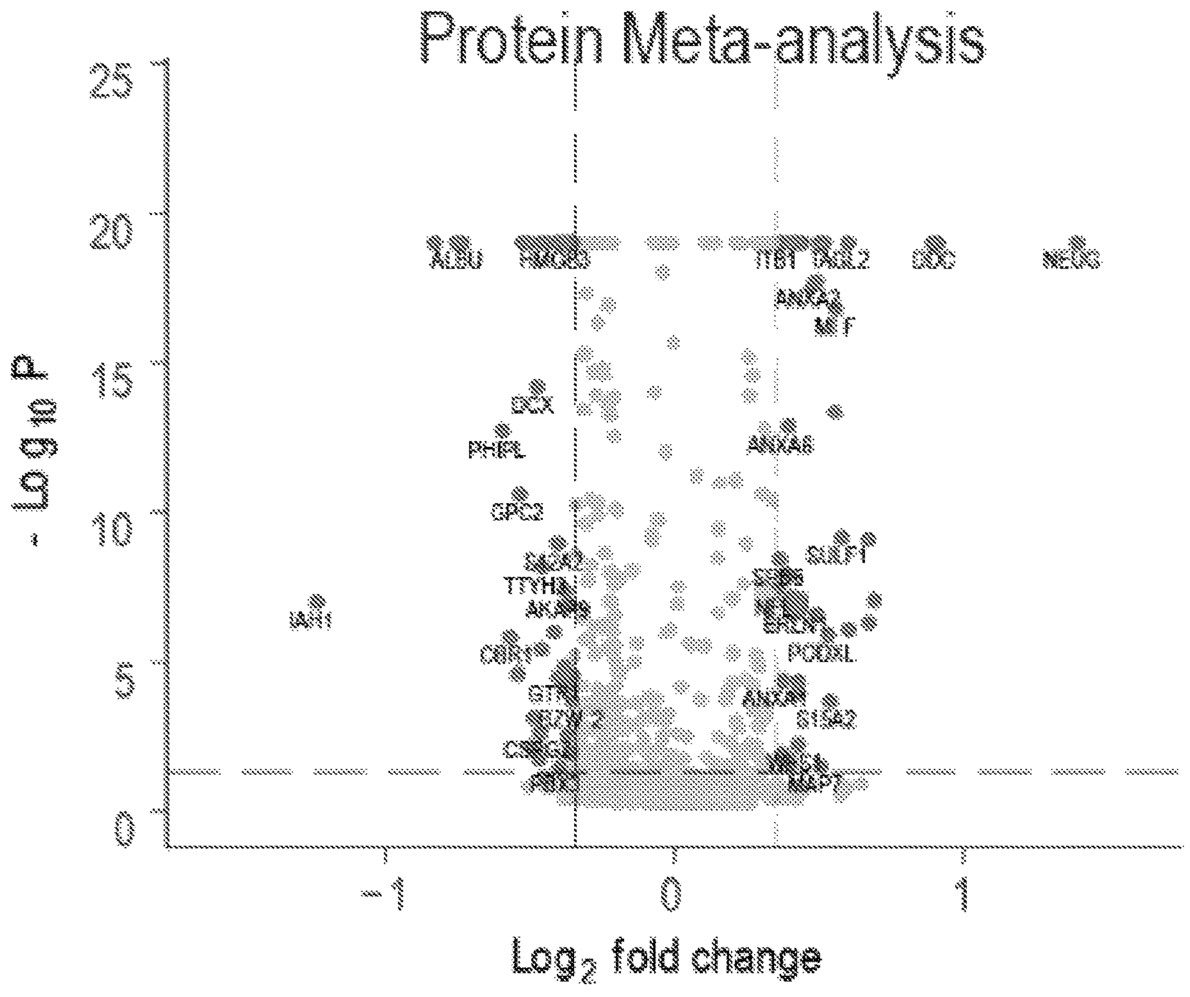
Figure 4:
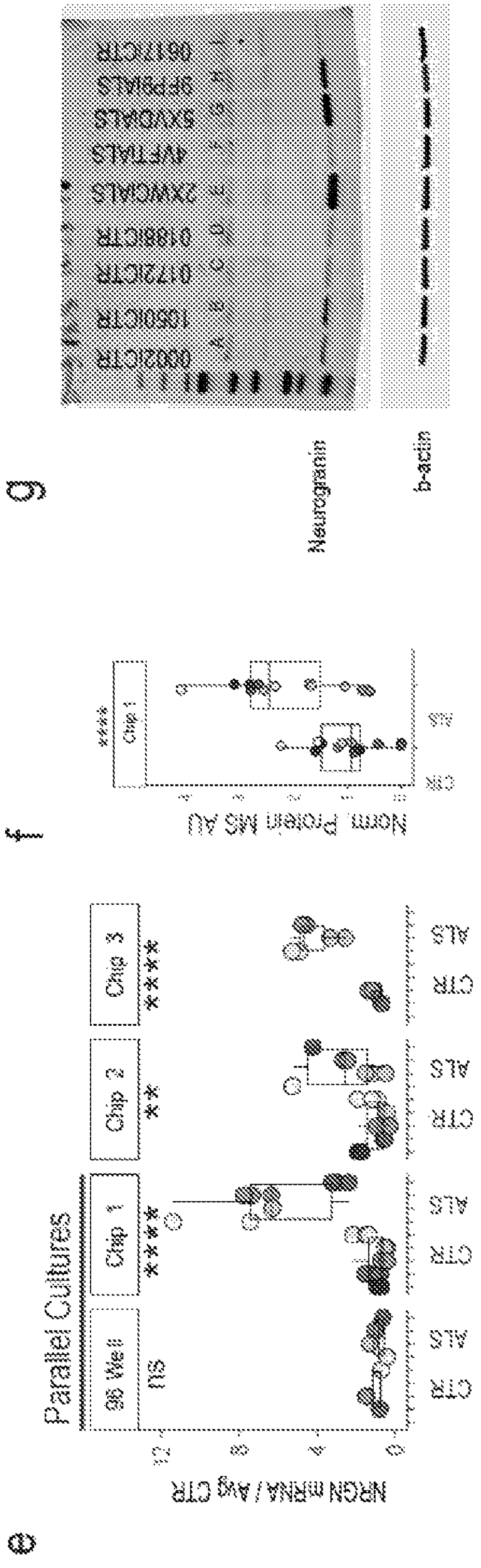

FIG. 4, panels a-g, depicts meta-analysis of replicate SC-chip studies identifies novel ALS biomarker candidates. (a) Volcano plot of differential expression calculated from three replicate chip studies combined. (b) Heatmap of top 40 differentially expressed genes ranked by adjusted p-value. (c) Volcano plot of averaged differential expression of two replicate protein studies. (d) Expanded table shows proteins calculated at minimum p-val (0) FDR and >0.35 log 2FC, and ranked by log odds ratio (see methods mapDIA). (e) Boxplot of neurogranin transcript gene (NRGN) expression across three replicate studies and parallel 96-well plate. (f) Boxplot of neurogranin protein (NEUG) expression across two replicate protein studies. (g) Western blot of NEUG protein from second protein replicate study.

Figure 5:
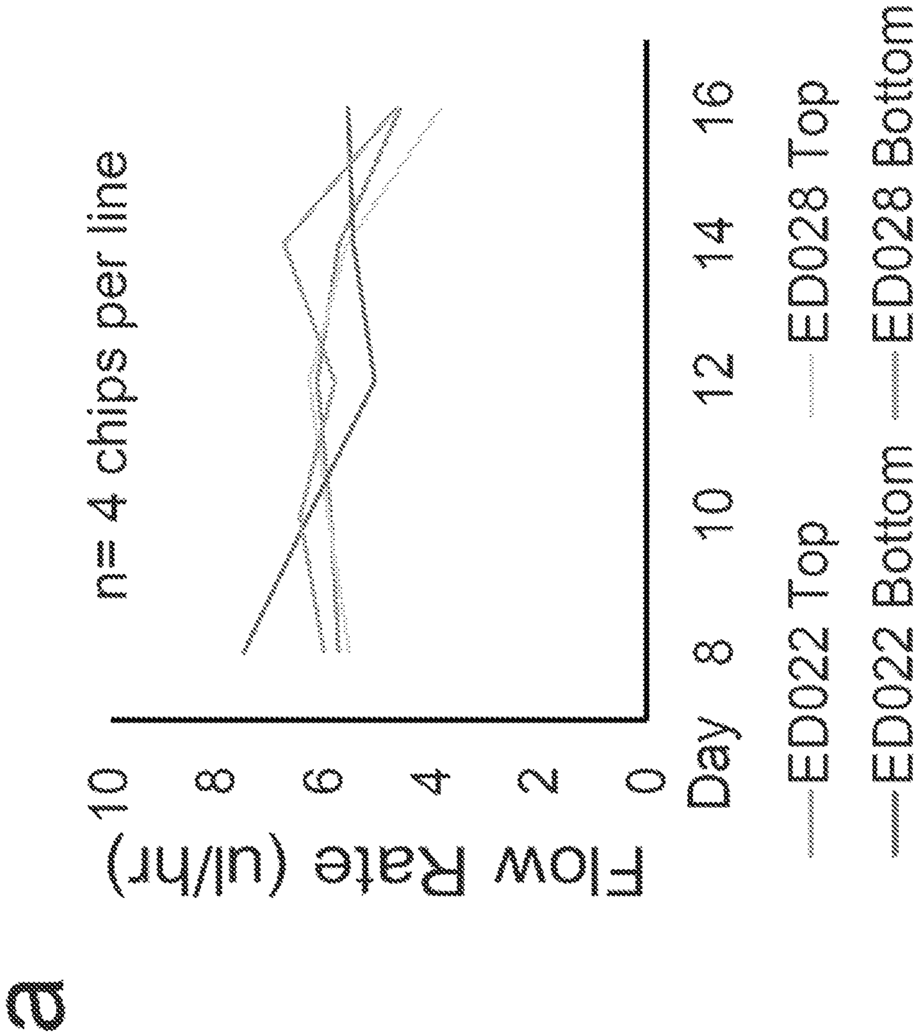
Figure 5:
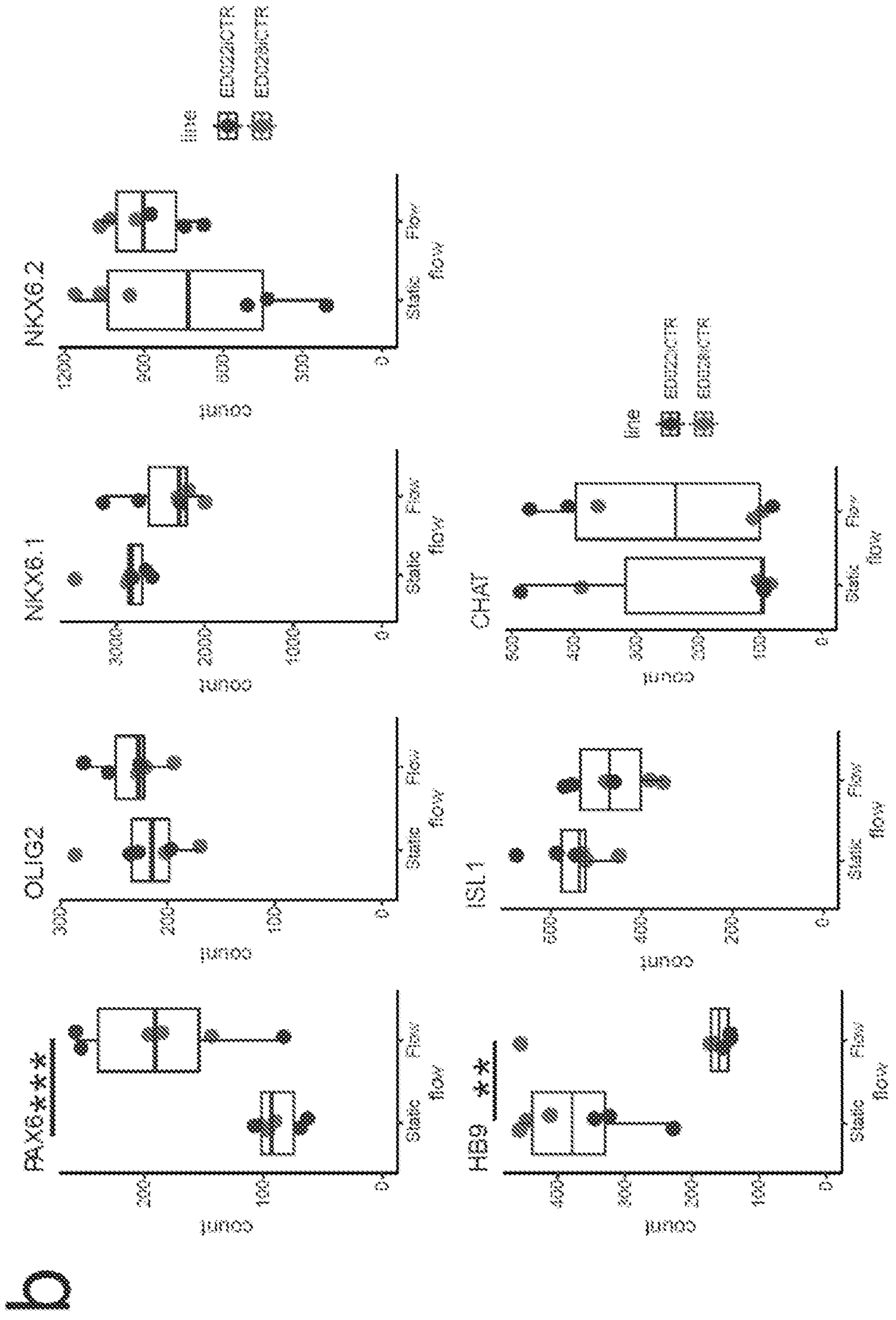

FIG. 5, panels a-c, depicts flow rates, boxplots, and pathway terms. (a) Flow rates of top and bottom channel over days 8-16 of chip culture. N=2 patient lines, 4 replicate chips per patient. (b) Boxplots of motor neuron related gene transcript counts. Significance calculated by Benjamini-Hochberg corrected Wald test correcting for all genes in dataset. (c) Gene set enrichment analysis (GSEA) gene ontology (GO) pathway terms generated from PC1 negative geneloading, ranked by Family wise error rate (FWER) p-values.

Figure 6:
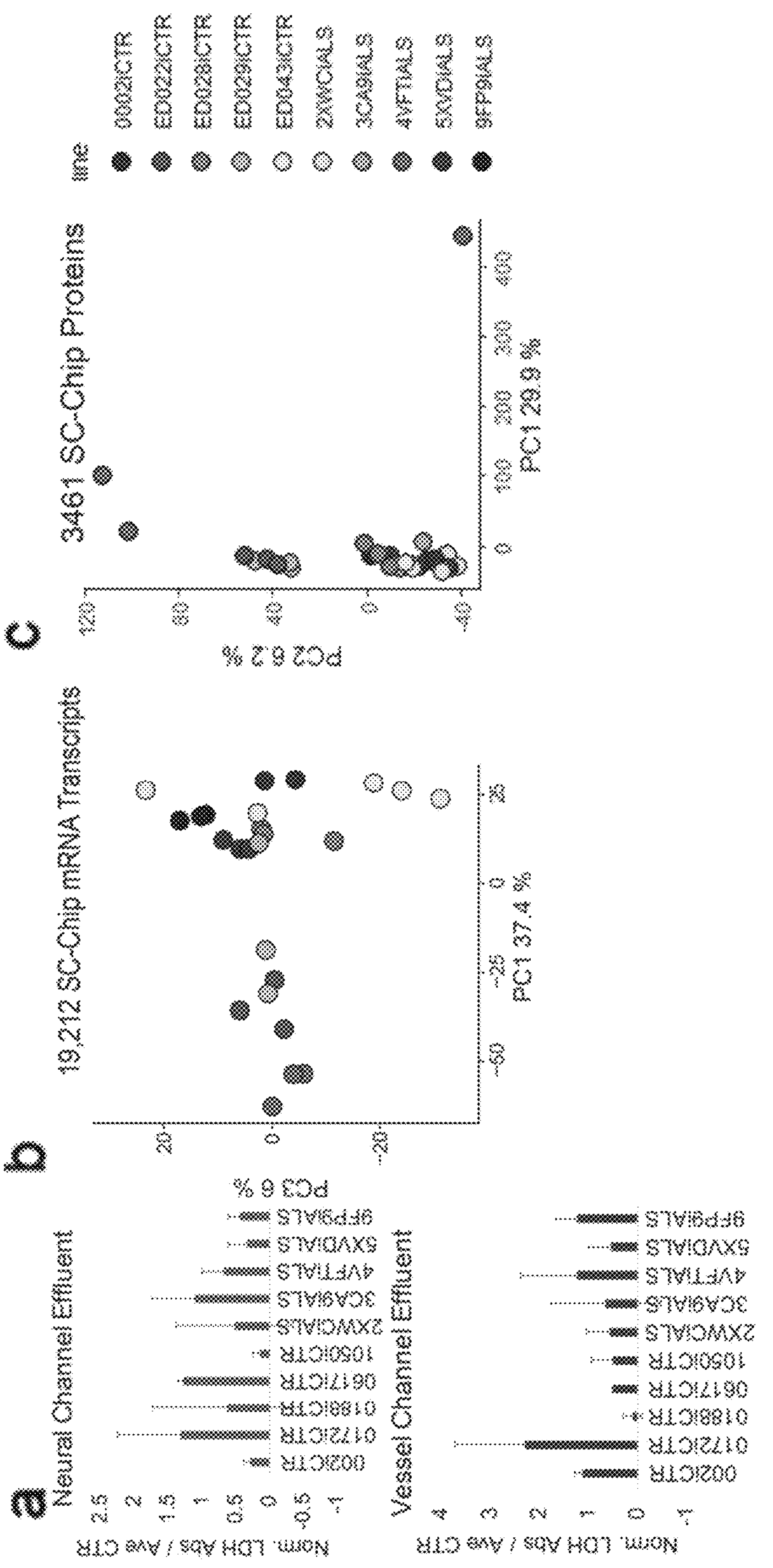
Figure 6:
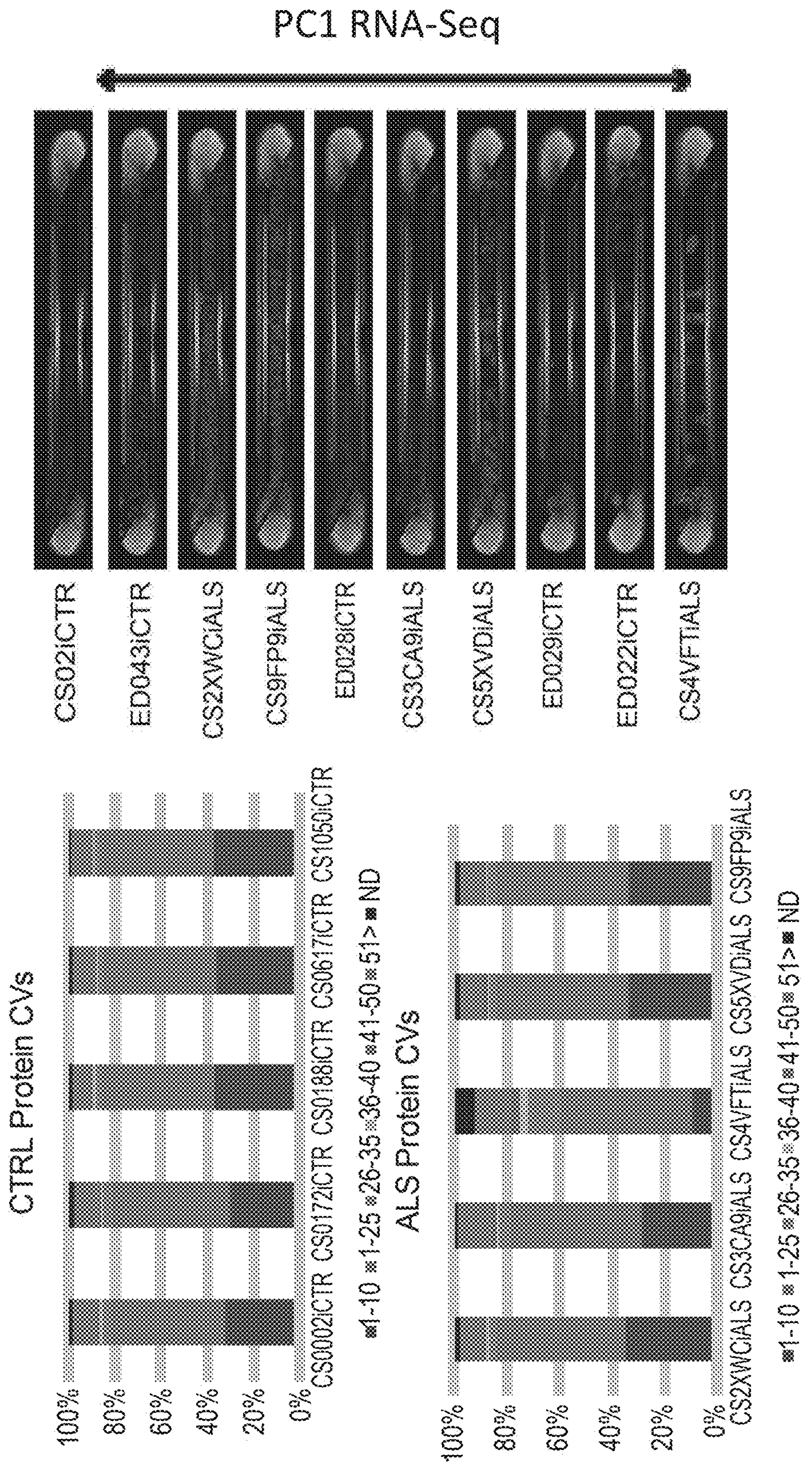

FIG. 6, panels a-f, depicts activity graphs, PCA plots, and heatmaps. (a) Lactate dehydrogenase activity graphs of neural and vascular channel effluents. (b, c) PCA plots of 10 lines from RNA (b) and protein (c). (d) Protein abundance coefficient of variance. (e) Representative stitched phase images of entire length of SC-chips at endpoint from each study. (f) Additional GSEA term heatmaps found in mRNA and Protein studies. Red color denotes up and blue color down (z-score).

Figure 7:
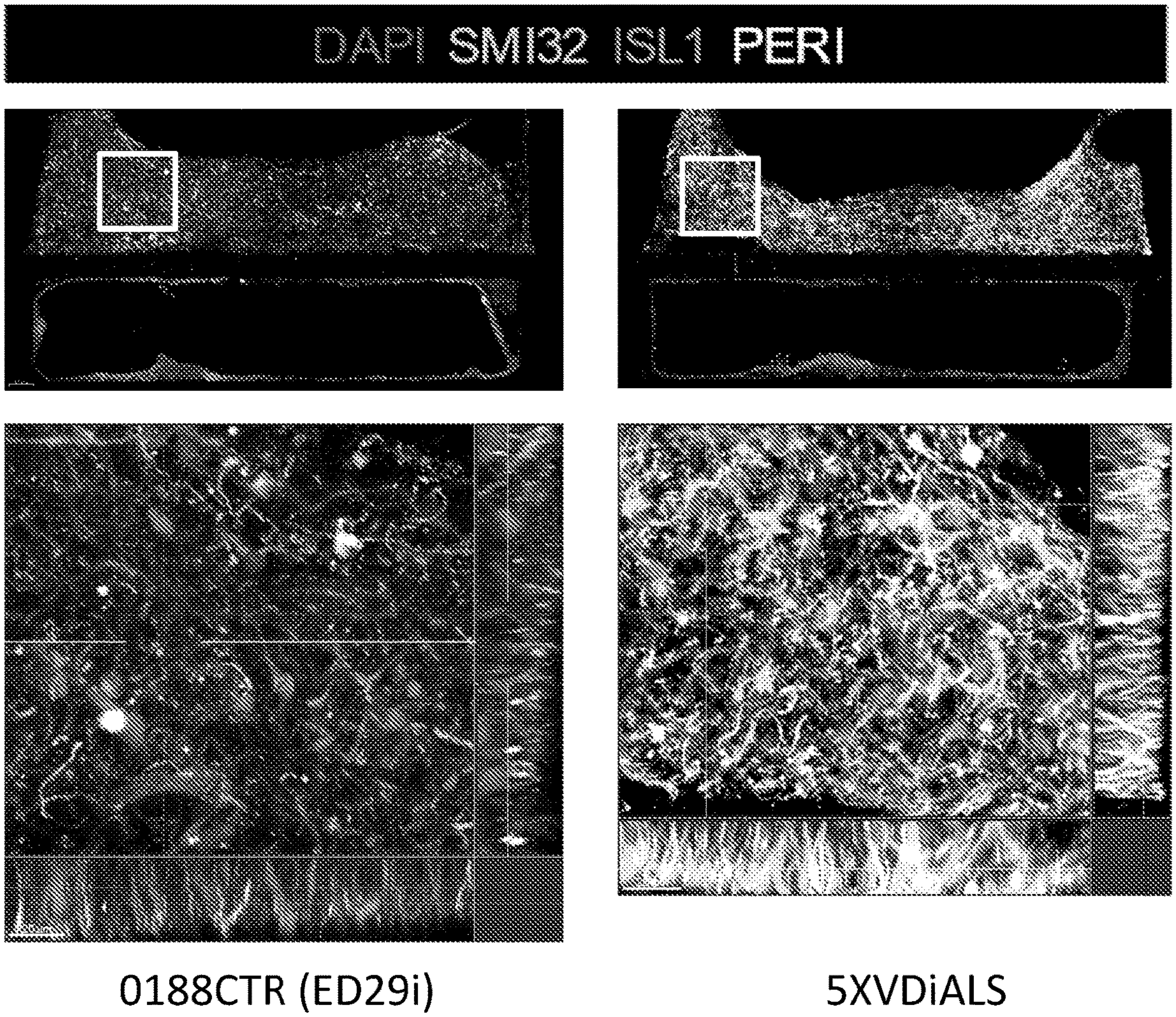

FIG. 7 depicts staining for neurofilaments (SMI32) is more pronounced in the SC-Chip from ALS subject indicating increased expression of NFH, and NFM. Peripherin (white) projections are also observed in higher quantity and intensity in the ALS subject ship section. ISL1 (red nuclei) marks motor neurons identified by co-labeling of SMI32 and ISL1.

DETAILED DESCRIPTION

All references cited herein are incorporated by reference in their entirety as though fully set forth. Unless defined otherwise, technical and scientific terms used herein have the same meaning as commonly understood by one of ordinary skill in the art to which this invention belongs.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used herein the term "about" when used in connection with a referenced numeric indication means the referenced numeric indication plus or minus up to 5% of that referenced numeric indication, unless otherwise specifically provided for herein. For example, the language "about 50%" covers the range of 45% to 55%. In various embodiments, the term "about" when used in connection with a referenced numeric indication can mean the referenced numeric indication plus or minus up to 4%, 3%, 2%, 1%, 0.5%, or 0.25% of that referenced numeric indication, if specifically provided for in the claims.

The initial symptom onset of ALS occurs at a median age of 65 years of age, with variable regionalization and progression rate. A juvenile form of the disease is associated with a positive family history and slow progression. A separate, "young-onset" form of ALS (YOALS) characterized by clinical onset at <45 years of age, follows progression and non-familial majority that closely resembles classical descriptions of the disease. We selected YOALS to determine disease specific signatures in SC-Chips, and find pronounced dysregulation of protein homeostasis and specifically increased levels of NFH and PERI gene expression.

Described herein is clinically-relevant model for ALS, a system comprising a device (for example, multi-channel 3-dimenional cell culture chip) and media that can reproduce key neurofilament signatures, which is a hallmark classifier for ALS. This device can be used to test drugs for efficacy and also test whether the drugs can cross the blood brain barrier (BBB). These neurofilament signatures are specific to the device; while not wishing to be bound by any particular theory, the inventors believe that they likely arise from the geometry of the device as well as the media flow, and are not observed in well plate experiments.

The sporadic nature of the disease model from young onset patients is novel. Since their clinical profile closely matches average sporadic patients, there is wide reaching potential for this system to be used to screen for and validate novel drugs for ALS.

The SC-Chip system of the present invention incorporates media perfusion, small 3D geometry and vascular interaction as a platform for human neurophysiology and disease. This system uniquely exhibits the NF phenotype where legacy systems such as 96 well plate do not. This was directly tested in parallel studies with 96 well and SC-Chip comparison of NF expression using the same starting diMN cultures. The system provides a platform for ALS study that incorporates a BBB and is capable of representing a large population of underserved patients.

Drug Screening

Various embodiments of the present invention provide for a method of identifying an agent of interest, comprising: contacting a quantity of neurons or a quantity of ventralized spinal motor neuron progenitor cells (spNPCs) with a test agent; measuring one or more parameters relating to the quantity of neurons or the quantity of ventralized spNPCs; and identifying the test agent as the agent of interest if the test agent modulates the one or more parameters, wherein the quantity of neurons or the quantity of spNPCs is differentiated from induced pluripotent stem cells (iPSCs). In various embodiments, the one or more parameters is 2, 3, 4, 5, 6, 7, 8, 9, 10, 11, 12, 13, 14, 15, 16, 17, 18, 19, or 20 parameters. In various embodiments, the one or more parameters is 1-5, 6-10, 11-15, 16-20, 21-25, 26-30, 31-35, or 36-40 parameters. In various embodiments, the one or more parameters is about 1-10 parameters. In various embodiments, the one or more parameters is about 11-20 parameters. In various embodiments, the one or more parameters is about 21-30 parameters. In various embodiments, the one or more parameters is about 31-40 parameters.

In various embodiments, the quantity of neurons or the quantity of spNPCs are in a top channel of a multi-channel 3-dimenional (3-D) cell culture chip.

In various embodiments, the method further comprises adding brain microvascular cells (BMECs) to a bottom channel of the multi-channel 3-D cell culture chip. In various embodiments, the method further comprises adding culture media to a bottom channel of the multi-channel 3-D cell culture chip. In various embodiments the culture media continuously flows through the bottom channel of the multi-channel 3-D cell culture chip.

In various embodiments, the neurons are spinal motor neurons.

In various embodiments, the iPSCs are from an amyotrophic lateral sclerosis (ALS) patient. In various embodiments, the iPSCs are from a sporadic ALS patient. In various embodiments, the iPSCs are from a young onset amyotrophic lateral sclerosis (YOALS) patient.

In various embodiments, the agent of interest is a drug for treating amyotrophic lateral sclerosis (ALS). In various embodiments, the agent of interest is a drug for treating young onset amyotrophic lateral sclerosis (YOALS). In various embodiments, the agent of interest is a drug that can cross the blood-brain barrier.

In various embodiments, the one or more parameters is expression level of one or more genes or one or more proteins, and the test agent is identified as the agent of interest if the test agent increases or decreases the expression level of one or more genes as compared to a reference level for each gene, or the test agent increases or decreases the expression level of one or more proteins as compared to a reference level for each protein.

In various embodiments, the one or more genes are selected from the group consisting of TOMM40L, BAX, RAC1, BAD, DAXX, PRPH2, GPX1, SOD1, PP3R2, CAT, MAP2K6, TNFRSF1A, NEFM, PRPH, NEFL, NEFH, and combinations thereof, and the test agent is identified as the agent of interest if the test agent increases or decreases the expression level of the one or more genes as compared to a reference level for each gene. In various embodiments, the one or more genes are 2, 3, 4, 5, 6, 7, 8, 9, 10, 11, 12, 13, 14, 15, or 16 of these genes. In various embodiments, the one or more genes are 1-5 of these genes. In various embodiments, the one or more genes are 6-10 of these genes. In various embodiments, the one or more genes are 11-16 of these genes.

In various embodiments, the one or more genes are selected from the group consisting of TOMM40L, BAX, RAC1, BAD, DAXX, PRPH2, GPX1, SOD1, PP3R2, CAT, MAP2K6, TNFRSF1A, NEFM, PRPH, NEFL, NEFH, NRGN, and combinations thereof, and the test agent is identified as the agent of interest if the test agent increases or decreases the expression level of the one or more genes as compared to a reference level for each gene. In various embodiments, the one or more genes are 2, 3, 4, 5, 6, 7, 8, 9, 10, 11, 12, 13, 14, 15, 16 or 17 of these genes. In various embodiments, the one or more genes are 1-5 of these genes. In various embodiments, the one or more genes are 6-10 of these genes. In various embodiments, the one or more genes are 11-17 of these genes.

In various embodiments, the one or more genes are selected from the group consisting of neurofilament light (NEFL), neurofilament medium (NEFM), neurofilament heavy (NEFH), peripherin (PRPH), neuronal microtubule gene beta 3 tubulin (TUBB3), and combinations thereof, and the test agent is identified as the agent of interest if the test agent increases or decreases the expression level of the one or more genes as compared to a reference level for each gene. In various embodiments, the one or more genes are 2, 3, 4, or 5 of these genes. In various embodiments, the one or more genes are 2-3 these genes. In various embodiments, the one or more genes are 4-5 of these genes.

In various embodiments, the one or more genes are neurofilament light (NEFL), neurofilament medium (NEFM), neurofilament heavy (NEFH), and peripherin (PRPH), and the test agent is identified as the agent of interest if the test agent increases or decreases the expression level of the one or more genes as compared to a reference level for each gene.

In various embodiments, the one or more proteins are selected from the group consisting of CCS, SLS1A2, PPP2CB, BCL2L1, RAC1, PPP3R1, SOD1, TOMM40, GPX1, CAT, MAPK14, NEFH, NEFM, NEFL, PRPH, and combinations thereof, and the test agent is identified as the agent of interest if the test agent increases or decreases the expression level of one or more proteins as compared to a reference level for each protein. In various embodiments, the one or more proteins are 2, 3, 4, 5, 6, 7, 8, 9, 10, 11, 12, 13, 14, or 15 of these proteins. In various embodiments, the one or more proteins are 1-5 of these proteins. In various embodiments, the one or more proteins are 6-10 of these proteins. In various embodiments, the one or more proteins are 11-15 of these proteins.

In various embodiments, the one or more proteins are selected from the group consisting of CCS, SLS1A2, PPP2CB, BCL2L1, RAC1, PPP3R1, SOD1, TOMM40, GPX1, CAT, MAPK14, NEFH, NEFM, NEFL, PRPH, NEUG and combinations thereof, and the test agent is identified as the agent of interest if the test agent increases or decreases the expression level of one or more proteins as compared to a reference level for each protein. In various embodiments, the one or more proteins are 2, 3, 4, 5, 6, 7, 8, 9, 10, 11, 12, 13, 14, 15, or 16 of these proteins. In various embodiments, the one or more proteins are 1-5 of these proteins. In various embodiments, the one or more proteins are 6-10 of these proteins. In various embodiments, the one or more proteins are 11-16 of these proteins.

In various embodiments, the one or more proteins are selected from the group consisting of neurofilament light (NFL), neurofilament medium (NFM) and neurofilament heavy (NFH), peripherin (PERI), neuronal microtubule gene beta 3 tubulin (TBB3) protein, and combinations thereof, and the test agent is identified as the agent of interest if the test agent increases or decreases the expression level of one or more proteins as compared to a reference level for each protein. In various embodiments, the one or more proteins are 2, 3, 4, or 5 of these proteins. In various embodiments, the one or more proteins are 1-3 of these proteins. In various embodiments, the one or more proteins are 4-5 of these proteins.

In various embodiments, the one or more proteins are neurofilament light (NFL), neurofilament medium (NFM), neurofilament heavy (NFH), and peripherin (PERI), the test agent is identified as the agent of interest if the test agent increases or decreases the expression level of one or more proteins as compared to a reference level for each protein.

In various embodiments, the method further comprises first generating the neurons or ventralized spNPCs before contacting a quantity of neurons or a quantity of ventralized spinal motor neuron progenitor cells (spNPCs) with a test agent. Generating the neurons can be performed by the inventive methods as described herein.

The reference level used in these methods can depend on the type of disease or condition that will be determined. Different types of diseases and conditions (e.g., different types of ALS—sporadic, young onset, hereditary) may have different reference levels. In various embodiments, each reference level is the expression level of each gene or each protein prior to contact with the test agent. In various embodiments, each reference level is the expression level of each gene or each protein that has not been contacted with the test agent.

In some embodiments, the reference level for each gene or protein can be established from biological samples from a healthy subject. For example, if the biological sample is a quantity of neurons, then the reference level can be obtained from the neurons of a healthy subject or neurons differentiated from iPSCs of healthy subject (e.g., subjects who do not have ALS or do not have family member who have ALS, or both). In other embodiments, the reference level is the average expression level for the same type of biological sample from a population of healthy subjects. In other embodiments, the reference level is the average plus one or two standard deviations of average expression level for the same type of biological sample from a population of healthy subjects. In some embodiments, the population of healthy subjects to establish the average can range from at least three healthy individuals to 25 healthy individuals, and even more than 50 healthy individuals.

In various embodiments, the multi-channel 3-dimenional (3-D) cell culture chips used in these methods are described in PCT/US2016/57724 filed Oct. 19, 2016, PCT/US2017/049193 filed Aug. 29, 2017, or PCT/US2019/026195 filed Apr. 5, 2019, the entirety of each which is herein incorporated by reference as though fully set forth. In various embodiments, the multi-channel 3-dimenional (3-D) cell culture chips are those made by, for example, Elveflow, Mimetas, Fluigent, Emulate, Inc., Organovo, BioIVT, Hurel Corporation, Nortis, TissUse, AxoSim, or Tara Biosystems. In various embodiments, the multi-channel 3-dimenional (3-D) cell culture chips used in these methods can be made by Emulate.

Systems

Various embodiments of the present invention provide for a system, comprising: a multi-channel 3-dimenional cell culture chip; a quantity of neurons or a quantity of ventralized spinal motor neuron progenitor cells (spNPCs); and cell culture media. Nonlimiting uses of the system include drug development, drug screening, disease study (e.g., ALS model, young onset ALS model, sporadic ALS model), including personalized form of these aforementioned uses (e.g., cells including iPSCs are from a patient for which the drug development, screening or disease study is made).

In various embodiments, the neurons are spinal motor neurons.

In various embodiments, the system further comprises a test agent.

In various embodiments, the quantity of neurons or the quantity of spNPCs is differentiated from induced pluripotent stem cells (iPSCs). In various embodiments, the iPSCs are from an ALS patient. In various embodiments, the iPSCs are from a sporadic ALS patient. In various embodiments, the iPSCs are from a young onset ALS patient.

In various embodiments, the multi-channel 3-dimenional (3-D) cell culture chips used in these systems are described in PCT/US2016/57724 filed Oct. 19, 2016, PCT/US2017/049193 filed Aug. 29, 2017, or PCT/US2019/026195 filed Apr. 5, 2019, the entirety of each which is herein incorporated by reference as though fully set forth. In various embodiments, the multi-channel 3-dimenional (3-D) cell culture chips are those made by, for example, Elveflow, Mimetas, Fluigent, Emulate, Inc., Organovo, BioIVT, Hurel Corporation, Nortis, TissUse, AxoSim, or Tara Biosystems. In various embodiments, the multi-channel 3-dimenional (3-D) cell culture chips used in these methods can be made by Emulate.

Generating Spinal Motor Neurons

Various embodiments of the present invention provide for a method generating spinal motor neurons, comprising: coating a top channel of a multi-channel 3-dimenional (3D) cell culture chip with substrate for culturing cells, coating a bottom channel of the multi-channel 3D cell culture chip with a mixture comprising collagen IV, fibronectin, and water; seeding the top channel with ventralized spinal motor neuron progenitor cells (spNPCs), wherein the ventralized spNPCs are in a media comprising IMDM/F12, B27, N2, NEAA, ascorbic acid, retinoic acid, cAMP, SAG, glial cell line-derived neutrotrophic factor, brain derived neutrotrophic factor, penicillin-streptavidin (PSA), and about 10 μM Y-27632; and culturing the ventralized spNPCs to differentiate them into spinal motor neurons. These spinal motor neurons can be useful for an amyotrophic lateral sclerosis (ALS) model (e.g., young onset or sporadic).

In various embodiments, the media comprises IMDM/F12, B27, N2, about 1% NEAA, about 200 ng/ml ascorbic acid, about 0.5 μM retinoic acid, about 0.1 μM cAMP, about 0.1 μM SAG, about 10 ng/ml glial cell line-derived neutrotrophic factor, about 10 ng/ml brain derived neutrotrophic factor, about 1% penicillin-streptavidin (PSA), and 10 μM Y-27632.

In various embodiments, the media comprises IMDM/F12, B27, N2, about 0.5-1.5% NEAA, about 100-300 ng/ml ascorbic acid, about 0.25-0.75 μM retinoic acid, about 0.05-0.15 μM cAMP, about 0.05-0.15 μM SAG, about 5-15 ng/ml glial cell line-derived neutrotrophic factor, about 5-15 ng/ml brain derived neutrotrophic factor, about 0.5-1.5% penicillin-streptavidin (PSA), and 5-15 μM Y-27632.

In various embodiments, the method further comprises flushing excess cells with the media without Y-27632 after about 1-3 hours of incubation. In various embodiments, the method further comprises flushing excess cells with the media without 10 μM Y-27632 after about 2 hours of incubation.

In various embodiments, culturing the ventralized spNPCs to differentiate them into spinal motor neurons comprises continuously perfusing the media through the top or the bottom channel to differentiate ventralized spNPCs into spinal motor neurons.

In various embodiments, the substrate for culturing cells is MATRIGEL matrix.

In various embodiments, the ventralized spNPCs is differentiated from induced pluripotent stem cells (iPSCs). In various embodiments, the ventralized spNPCs is differentiated from iPSCs from an ALS patient. In various embodiments, the ventralized spNPCs is differentiated from iPSCs from a sporadic ALS patient. In various embodiments, the ventralized spNPCs is differentiated from iPSCs from a young onset ALS patient.

In various embodiments, the multi-channel 3-dimenional (3-D) cell culture chips used in these methods are described in PCT/US2016/57724 filed Oct. 19, 2016, PCT/US2017/049193 filed Aug. 29, 2017, or PCT/US2019/026195 filed Apr. 5, 2019, the entirety of each which is herein incorporated by reference as though fully set forth. In various embodiments, the multi-channel 3-dimenional (3-D) cell culture chips are those made by, for example, Elveflow, Mimetas, Fluigent, Emulate, Inc., Organovo, BioIVT, Hurel Corporation, Nortis, TissUse, AxoSim, or Tara Biosystems. In various embodiments, the multi-channel 3-dimenional (3-D) cell culture chips used in these methods can be made by Emulate.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1A

Methods

Donor iPSC Reprogramming, Maintenance and Differentiation Into Spinal NPCs and BMECs iPSC reprogramming of young onset sporadic ALS patients was conducted as published previously.

Each cell type was qualified for use in studies as containing motor neurons (identified by Isl-1/SMI32 co-expression), and >1000 ohms/sq cm trans endothelial electrical resistance for BMECs.

Chip Culture:

PDMS U-1 Chips (Emulate) were washed with ethanol and treated with surface activator ER1 (Emulate) and activation with Ultraviolet light. Chips were washed and immediately coated with Matrigel (Corning) on the top channel and a 4:1:45 mixture of collagen IV (Sigma), fibronectin (Invitrogen), and water on the bottom channel and left overnight at 37° C. and 5% $CO_2$. spNPCs were thawed and seeded into the top channel at a density of 12E6 cells/ml in stage 3 media consisting of IMDM/F12 (Gibco), B27, N2, 1% NEAA, 200 ng/ml ascorbic acid, 0.5 μM retinoic acid, 0.1 μM cAMP, 0.1 μM SAG, 10 ng/ml glial cell line-derived neutrotrophic factor, 10 ng/ml brain derived neutrotrophic factor, 1% penicillin-streptavidin (PSA), 10 μM Y-27632) and excess cells were flushed with stage 3 media without 10 μM Y-27632 after 2 hours of incubation.

Cell Population Analysis From Immunostaining.

MKI67 population counts were generated from images taken on a Nikon A1R confocal microscope of an intact chip at 10×. 3 sites from each chip were acquired and analyzed using the spots function for mean 647 channel intensity on IMARIS (Bitplane).

RNA-Seq Analysis

Chips were cultured to endpoint as described above. At endpoint, the top channels all chip samples were incubated with cold Accutase (STEMCELL Technologies) for 20 minutes at 37° C., then neural tissue was extracted by flushing cold phosphate buffered saline (PBS), pelleted by centrifuge at 350 rcf, and frozen at −80° C. Total RNA extraction was conducted using RNAeasy mini kit (Qiagen) for whole chips with 100 ng input for RNA Sequencing using TruSeq mRNA-Seq library preparation kit. For the second and third replicate ALS cohort studies, chips were halved before extraction to allow multiple downstream analyses. Chip half RNA were extracted from pellets using RNAeasy micro (Qiagen) with 7 ng and 10 ng RNA used as input for studies two and three respectively. SMART-Seq V4 ultra low input RNA kit (Takara bio) and Nextera XT library kit (Illumina) was used for sequencing. All sequencing was conducted on the NovaSeq at 1×75 bp with at least 40 million reads per sample. Reads were mapped using Salmon VXXX, transcripts were collapsed to Ensembl gene IDs using tximeta R package. Genes present (count>=1) in less than 50% of chips were discarded.

Differential expression analysis and normalization was conducted using DESeq2 V1.26.0. For PCA analysis, count matrices were normalized using variance stabilization transformation and limma batch correction was used to align whole and half chip preparations from the three replicate studies.

Flowrate Analysis

Average flowrate was calculated by an average outflow over time. Chip PODs were fed with 3 ml on the inlet channel and media was completely removed from outlet channel. 48 hrs later, effluent volume was weighed and volume was calculated as 1 ml/mg and divided by 48 hrs for a rate per hour. Volume effluent across 5 timepoints in all 4 chips per condition. The total volume difference between initial and final volume across chips had an average of 282 uL+/−10 uL representing <1% of the total volume added in the inlet reservoir.

Example 1 B

Results

The inclusion of media flow in iPSC-derived neuronal cultures has not been fully explored. We wondered if continuous media perfusion would stimulate spinal cord chip development, which in turn could be used as an advanced substrate for young onset ALS disease studies in vitro. To determine the effects of flow directly on vascularized spinal cord tissue chips, two donor iPSC lines (ED022 and ED028) were differentiated into ventralized spinal motor neuron progenitor cells (spNPCs) and cryogenically stored in a working lot for use in tissue chip studies. Brain microvascular cells (BMECs) were differentiated from a separate donor (02iCTR) line and cryogenically stored. Spinal NPCs from each were seeded from frozen stocks into the top "neural" channel of 6 identical chips made from polydimethylsiloxane (PDMS) containing two chambers separated by a porous membrane (Emulate Inc). After 14 days, BMECs were added to the bottom channel forming a continuous tube of vascular endothelium.

Figure 1:
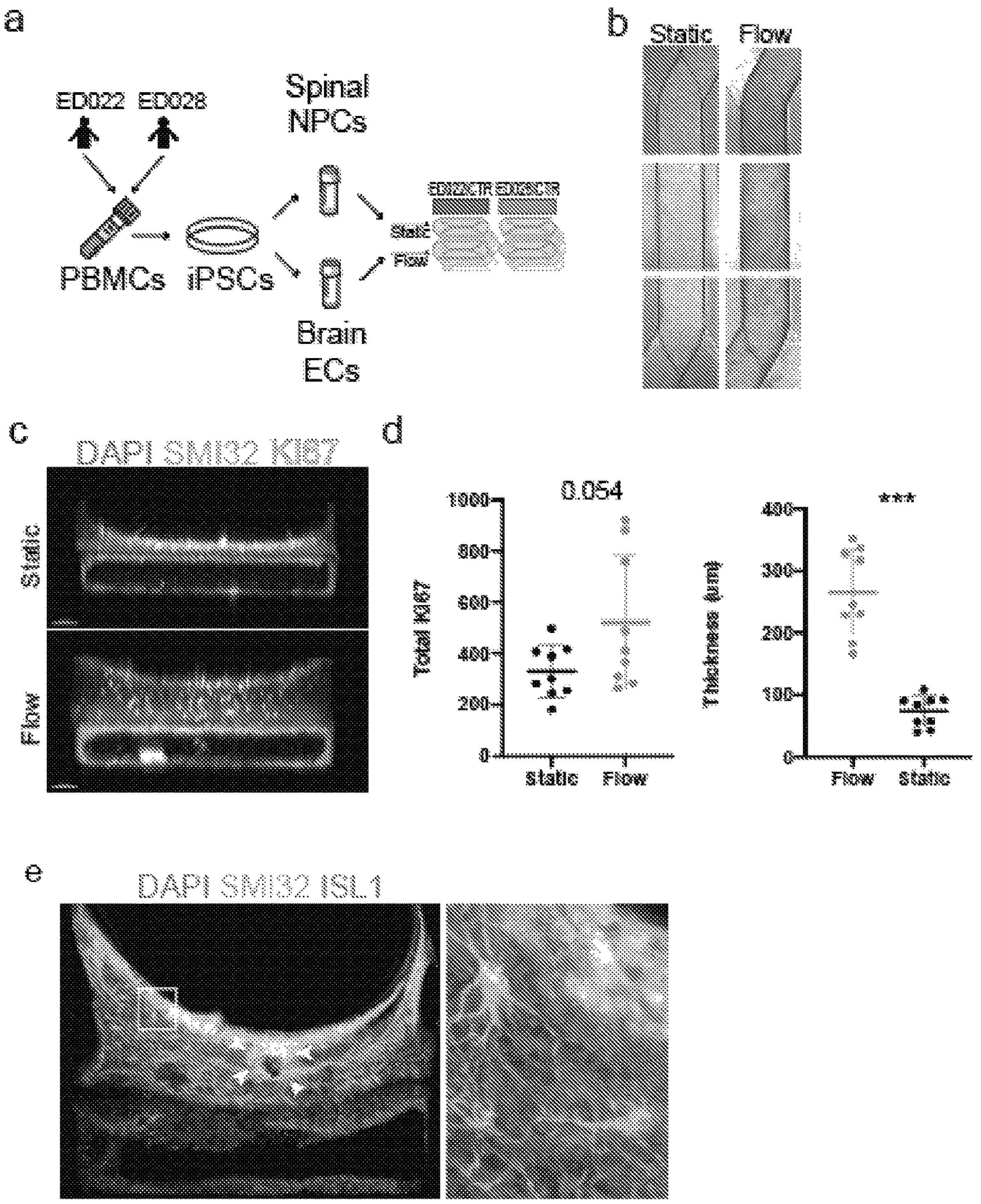
FIG. 1, panels a-i, depicts media perfusion increases spinal tissue growth and vascular recruitment. (a) Schematic of two patient peripheral blood mononucleocyte (PBMC) samples reprogrammed, differentiated to spinal neural progenitor cells (spNPCs) and brain microvascular endothelial cells (ECs), and cultured on chip replicates for 28 days. (b)
Figure 1:
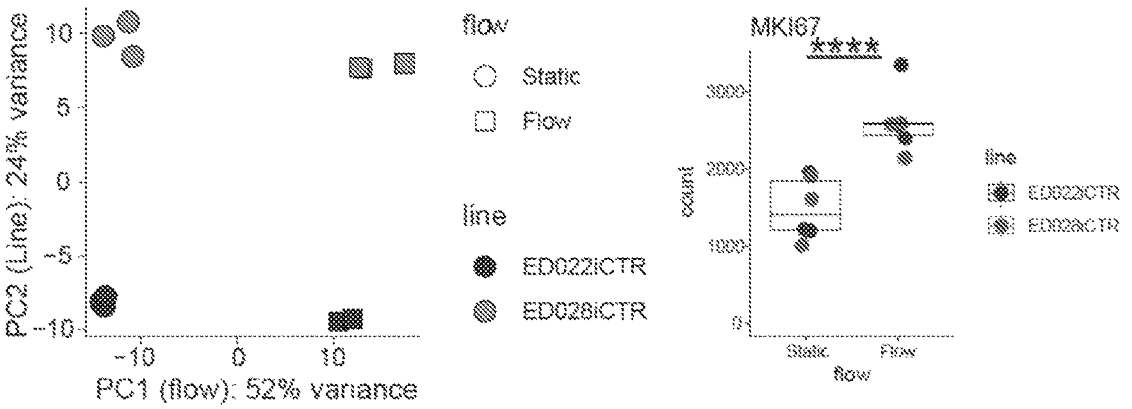
Figure 1:
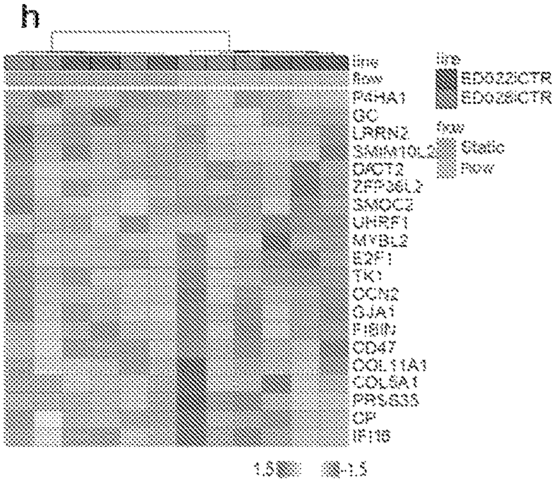
Figure 1:
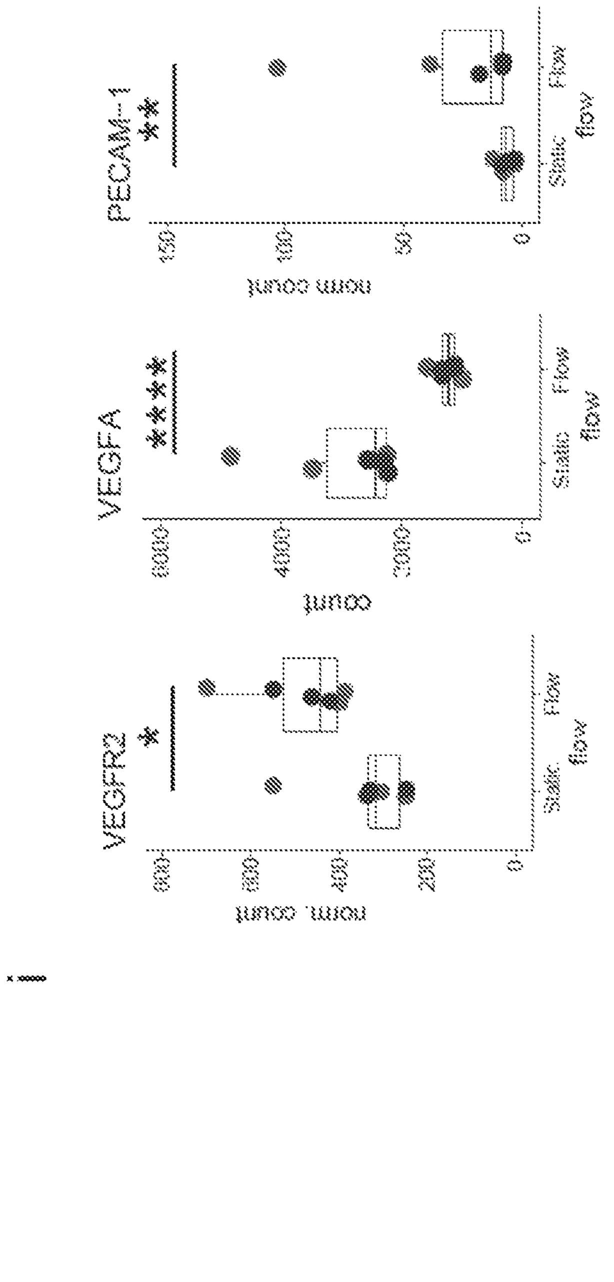

8 chips from each line were subdivided into two groups: static and flow. The static chips were flushed with fresh media every other day. The flow condition was administered for the duration of the study by hydrostatic force exerted by the weight of media in the input reservoir of a microfluidic cassette (POD, Emulate Inc.). An average perfusion rate across all 12 chips was 5.88 μl/hr (95% C.I. [5.53,6.21]) or one total neural volume change every 3.2 hours. (FIG. 5) At 28 days, the flow condition displayed pronounced tissue growth that could be observed by phase contrast (FIG. 1 (*b*)). To determine if tissue growth was due to increased proliferation, one chip from each group was fixed and immunostained (FIG. 1 (*b*) and (*e*)). Nuclear marker DAPI and proliferation marker Ki67 were significantly increased in the neural compartment of the flow condition Chips (FIG. 1 (*c*)). Immunocytochemical staining of cross sections from chips under flow revealed complex $SMI32^{+}/ISL1^{+}$ motor neurons residing within the developing 3D tissue. On the neural channel luminal surface, large $SMI32^{+}$ neurites tracked along the length of the chip (FIG. 1). Interestingly, clusters of $SMI32^{-}/ISL1^{+}$ cells were sometimes seen (FIG. 1 (*e*)) in the top channel of the chip, indicating putative BMEC infiltration. Increased $SMI32^{+}$ expression was also detected surrounding the $SMI32^{-}/ISL1^{+}$ cells (FIG. 1 (*e*) arrows).

To define the molecular responses resulting from constant media flow that contributed to the three-dimensional neuronal environment in the top channel of the SC-Chip, the experiment was repeated, and neural channel tissue was extracted from the top channel of each chip and processed for RNA-Sequencing. Significantly increased expression of proliferation marker gene MKI67 (Ki67) confirmed protein staining results. Expression of canonical motor neuron progenitor markers OLIG2, NKX6.1, NKX6.2, ISL1 and choline acetyltransferase (CHAT) were unchanged. However, early neural progenitor marker PAX6 was significantly increased while post-mitotic motor neuron transcription factor MNX1 (HB9) was significantly down regulated, indicating progenitor cells overtook mature motor neuron transcripts in the bulk culture (FIG. 5).

To assess major contributors of transcript expression variance across all samples, principle component (PC) analysis was performed (FIG. 1 (*f*)). The PC explaining the largest portion of variance (PC1) separated static from flow chips. PC2 segregated expression variance across the two donors. To determine how flow impacted general cellular functions, gene set enrichment analysis (GSEA) was conducted on a list of all genes ranked by geneloading along the PC1 "flow" axis (FIG. 1 (*f*)). Pathways related to cell proliferation such as GO_MITOTIC_CELL_CYCLE and GO_DNA_REPAIR accounted for a majority of the significantly upregulated pathways. Significantly enriched pathways in the non-flow condition consisted of neuronal machinery such as GO_SYNAPTIC_SIGNALLING supporting the interpretation of an enrichment of progenitors in the flow condition (FIG. 5). Flow enriched term GO_VASCULAR_DEVELOPMENT (P=0.001 FWER) included 6 of the top 20 differentially expressed genes (FIG. 5). We probed for Vascular endothelial growth factor receptor 2 (VEGFR2 also known as KDR), known to be required for vasculogenesis in vivo was significantly increased, however VEGF ligand VEGFA was significantly reduced in the neural channel tissue (FIG. 1 (*h*)). To confirm endothelial cell presence, pan-endothelial cell specific marker PECAM-1 gene expression was also probed and indicated significant increase in expression, indicating increased presence of endothelial cells in the neural tissue channel (FIG. 1 (*i*)). Taken together, these results indicated flow in the neuronal channel contributed to significant tissue growth through mitosis, extracellular matrix organization, and vasculogenesis.

We next sought to determine if the perfused spinal cord chip model could be used to determine disease specific signatures among sporadic ALS patients. While not wishing to be abound by any particular theory, we believed that by selecting for patients presenting with symptoms at an early age, referred to as young onset ALS (YOALS), the genetic contribution to their disease may be manifested in the SC-Chips. 5 Patient lines were selected from the ANSWER ALS repository of iPSCs and cultured in parallel with 5 control lines with no neurological deficit (FIG. 2). iPSCs from each line were simultaneously differentiated into spNPCs and cryogenically banked as before. The 10 lines were then thawed into 4 replicate chips per line and cultured under flow for 28 days (FIG. 2). BMECs from the 02iCTR line were added at day 14. To determine the specificity of the Chip environment compared to microwell-based monoculture, a 96-well plate was seeded in parallel and processed identically for each study. iPSC derived spinal motor neurons from sporadic ALS patients have been reported to exhibit increased levels of lactate dehydrogenase activity indicating disease specific cell death in vitro. However, no disease specific increase was observed in the SC-Chips from ALS patients in either neuronal or vascular channel effluents across the two studies (FIG. 5 (*a*)).

To discover active gene transcription activation and downstream protein expression, one chip was fixed and sectioned for immunostaining and 3 remaining chips were split in half and processed for either whole transcript or protein expression through mRNA-sequencing or SWATH proteomics respectively. Unsupervised PC analysis was conducted on each dataset, comprising of 19,212 transcripts and 2424 proteins passing quality filters. Clustering of patient line chip replicates indicated reproducible molecular signatures within chip replicates with the exception of 4VFTiALS Chips. Overall lower protein abundance in the 4VFTiALS line and phase images of chips at endpoint which showed distinct bunching that reflected both RNA and protein dataset variance indicated 4VFT as an outlier and the line was omitted from all subsequent analysis. PC analysis of the remaining chips separated ALS and control (CTR) lines along the third most significant PC (PC3) in both datasets with 7.9% and 9.9% of the variance in RNA and protein data respectively (FIG. 2 (*b*), (*c*)). To determine major cellular pathway contributors to the PC3 "ALS" axis, GSEA analysis was conducted with the curated KEGG gene set database using ranked geneweightings as before (FIG. 2 (*d*)). Strikingly, KEGG_AMYOTROPHIC_LATERAL_SCLEROSIS_ALS was significantly upregulated in both RNA and protein data. To determine pathways activated specifically in ALS chips, GSEA analysis was repeated in a supervised manner by calculating adjusted p-value gene rankings by differential expression analysis. Deseq2 in mRNA datasets and mapDIA in protein data.

Pathways were ranked by significance and adjusted by false discovery rate (FDR) (FIG. 2 (*d*)). Enrichment of cellular pathways from the mRNA transcript data was almost entirely in ALS patient samples (362:1). The most significant of these were related to protein translation including pathways overlapping with ribosomal complex and mRNA initiation complex, and endoplasmic reticulum transport. In addition, Pathways GO_CELL_CYCLE and GO_OXIDATIVE_PHOSPHORYLATION were significantly increased in the ALS patient chips. Conversely, no pathways were enriched in the ALS patient protein dataset. Instead, 22 pathways were significantly reduced $p<0.05$ FDR. GO_MITOCHONDRIAL_RESPORATORY_CHAIN_COMPLEX and GO_OXIDATIVE_PHOSPHORYLATION was reduced in the protein dataset, indicating a potential demand for the observed transcription increase (FIG. 2 (*d*)). In addition, terms related to synaptic machinery were also reduced in the ALS patient chips. To interrogate this dichotomy, a separate differential expression analysis was repeated on each dataset. 1241 significantly altered genes were detected in the mRNA data, and approximately half were upregulated in ALS. However, 92% of the differentially expressed proteins (1370/1478) were reduced in the ALS patient chips compared to non-diseased control lines, confirming pathway enrichment results.

To determine if the reduced presence of protein was due to increased degradation, we probed for marker genes of proteasomal and lysosomal activity. mRNA pathway analysis contained GO-REGULATION_OF_PROTEIN_UBIQUITINATION_DEPENDENT_PROTEIN_CATABOLIC_PROCESS led us to probe for components of the Ubiquitin complex. Of the 108 upregulated proteins, lysosome constituent LAMP1 was the third most significantly upregulated (FIG. 2). We confirmed increased LAMP1 expression by western blot. Taken together, the molecular profiling of the SC-Chips determined altered translational activity, metabolism, and degradation machinery specific to YOALS patients.

Clinical studies have documented neurofilament (NF) accumulation in the ventral horn of the spinal cord as specific biomarkers of ALS. NFH has also been detected in ALS patient cerebral spinal fluid (CSF) by ELISA and western blot. We noted a significant increase in NEFH transcripts and NFH protein in the SC-Chips (FIG. 3 (*a*), (*b*)). Upon immunostaining of chip cross-sections, increased levels of SMI32, an antibody recognizing phosphorylated NFH protein, was observed (FIG. 3 (*c*)). To quantify NFH protein expression, western blot on neural channel extracts was performed (FIG. 3 (*d*)). Peripherin is well characterized constituent of ubiquinated inclusions in the motor neurons of ALS patient spinal cords in post-mortem samples. Interestingly, identical spMNs cultured in 96-well plates did not exhibit significant increased expression of NEFH or PHSP, indicating the signature was specific to this system. We also noted Neurogranin (NRGN), a protein that has also been detected in Alzheimer's patient CSF, was upregulated in both mRNA transcripts and protein. We also confirmed increased Neurogranin protein by western blot (FIG. 3 (*d*)).

Referring to FIG. 6, using unsupervised gene expression analysis from the tissue grown in the SC-chip from ALS patients, a ALS-specifying genetic signature was identified. The genes relating to this signature in both gene transcript and proteins were then fed through a pathway analysis. The increase in gene expression from the ALS patients were found to reproduce known gene over expression that have been found in clinical spinal cord samples in post mortem ALS patients. This indicated that these signatures were implicated in ALS and specific to disease. It also implicates these genes as existing at the initial stage of disease in a controlled setting without additional environmental stressors.

Referring to FIG. 7, among the differentially expressed genes found to specify the ALS patient SC-Chips, were neurofilament gene family members. These genes have been described as abhorrently expressed in patient spinal cords and are a hallmark pathology used for definitive diagnosis post mortem. SC-Chips reproducing this phenomenon from induced pluripotent stem cell derived tissues show these genes to be implicated in the initial stages of the disease and can be corrected though drug screening to determine potential therapeutics for ALS.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

What is claimed is:

1. A method of identifying an agent of interest, comprising:

contacting a quantity of neurons or a quantity of ventralized spinal motor neuron progenitor cells (spNPCs) with a test agent in a top channel of a multi-channel 3-dimenional (3-D) cell culture chip;

adding brain microvascular cells (BMECs) to a bottom channel of the multi-channel 3-D cell culture chip;

adding culture media to the bottom channel, causing the culture media to continuously perfuse through the top or bottom channel;

measuring biomarkers of amyotrophic lateral sclerosis (ALS) comprising one or more parameters relating to the quantity of neurons or the quantity of ventralized spNPCs, the one or more parameters being expression level of one or more genes or one or more proteins; and identifying the test agent as the agent of interest if the test agent modulates the one or more parameters by increasing or decreasing the expression level of one or more genes as compared to a reference level for each gene, or by increasing or decreasing the expression level of one or more proteins as compared to a reference level for each protein, wherein the quantity of neurons or the quantity of spNPCs is differentiated from induced pluripotent stem cells (iPSCs) from an ALS patient.

2. The method of claim 1, wherein the neurons are spinal motor neurons.

3. The method of claim 1, wherein the ALS patient is a young onset amyotrophic lateral sclerosis (YOALS) patient.

4. The method of claim 3, wherein the agent of interest is a drug for treating amyotrophic lateral sclerosis (ALS).

5. The method of claim 3, wherein the agent of interest is a drug for treating young onset amyotrophic lateral sclerosis (YOALS).

6. The method of claim 1, wherein the agent of interest is a drug that can cross the blood-brain barrier.

7. The method of claim 1, wherein the one or more parameters is expression level of one or more genes or one or more proteins, and the test agent is identified as the agent of interest if the test agent increases or decreases the expression level of one or more genes as compared to a reference level for each gene, or the test agent increases or decreases the expression level of one or more proteins as compared to a reference level for each protein.

8. The method of claim 7, wherein the one or more genes are selected from the group consisting of TOMM40L, BAX, RACI, BAD, DAXX, PRPH2, GPX1, SOD1, PP3R2, CAT, MAP2K6, TNFRSF1A, NEFM, PRPH, NEFL, NEFH, and combinations thereof, and the test agent is identified as the agent of interest if the test agent increases or decreases the expression level of the one or more genes as compared to a reference level for each gene.

9. The method of claim 7, wherein the one or more genes are selected from the group consisting of neurofilament light (NEFL), neurofilament medium (NEFM), neurofilament heavy (NEFH), peripherin (PRPH), neuronal microtubule gene beta 3 tubulin (TUBB3), and combinations thereof, and the test agent is identified as the agent of interest if the test agent increases or decreases the expression level of the one or more genes as compared to a reference level for each gene.

10. The method of claim 7, wherein the one or more genes are neurofilament light (NEFL), neurofilament medium (NEFM), neurofilament heavy (NEFH), and peripherin (PRPH), and the test agent is identified as the agent of interest if the test agent increases or decreases the expression level of the one or more genes as compared to a reference level for each gene.

11. The method of claim 7, wherein the one or more proteins are selected from the group consisting of CCS, SLS1A2, PPP2CB, BCL2L1, RAC1, PPP3R1, SOD1, TOMM40, GPX1, CAT, MAPK14, NEFH, NEFM, NEFL, PRPH, and combinations thereof, and the test agent is identified as the agent of interest if the test agent increases or decreases the expression level of one or more proteins as compared to a reference level for each protein.

12. The method of claim 7, wherein the one or more proteins are selected from the group consisting of neurofilament light (NFL), neurofilament medium (NFM), neurofilament heavy (NFH), peripherin (PERI), neuronal microtubule gene beta 3 tubulin (TBB3) protein, and combinations thereof, and the test agent is identified as the agent of interest if the test agent increases or decreases the expression level of one or more proteins as compared to a reference level for each protein.

13. The method of claim 7, wherein the one or more proteins are neurofilament light (NFL), neurofilament medium (NFM), neurofilament heavy (NFH), and peripherin (PERI), and the test agent is identified as the agent of interest if the test agent increases or decreases the expression level of one or more proteins as compared to a reference level for each protein.

14. The method of claim 1, further comprising treating ALS patients with the identified agent of interest.

15. The method of claim 14, wherein the identified agent of interest is capable of crossing the blood-brain barrier.

16. The method of claim 1, wherein the quantity of neurons or the quantity of spNPCs differentiated from iPSCs from the ALS patients exhibits a significant increase in neurofilament heavy (NEFH) transcripts and neurofilament heavy (NFH) protein in the 3-D cell culture chip, compared to non-diseased control lines.

17. The method of claim 1, wherein the BMECs are added to the bottom channel 14 days after adding the quantity of neurons or the quantity of spNPCs to the top channel.

18. A system, comprising:

a multi-channel 3-dimenional (3-D) cell culture chip having:

a top channel including a quantity of neurons or a quantity of ventralized spinal motor neuron progenitor cells (spNPCs) for contacting a test agent; and a bottom channel including brain microvascular cells (BMECs) and cell culture media, wherein the quantity of neurons or the quantity of spNPCs is differentiated from induced pluripotent stem cells (iPSCs) from an amyotrophic lateral sclerosis (ALS) patient, and wherein the system is configured to perfuse the cell culture media continuously through the top or bottom channel.

19. The system of claim 18, wherein the neurons are spinal motor neurons.

20. The system of claim 18, further comprising a test agent.

21. The system of claim 18, wherein the ALS patient is a young onset amyotrophic lateral sclerosis (YOALS) patient.

22. The system of claim 18, wherein the multi-channel 3-D cell culture chip contains increased neurofilament expression.

* * * * *